United States Patent
Schewe et al.

(10) Patent No.: US 6,734,340 B2
(45) Date of Patent: May 11, 2004

(54) MONOCOTYLEDON PLANT CELLS AND PLANTS WHICH SYNTHESISE MODIFIED STARCH

(75) Inventors: Gabi Schewe, Hamburg (DE); Petra Knies, Hamburg (DE); Simeone Franceska Amati, Hamburg (DE); Horst Lorz, Hamburg (DE); Drik Becker, Hamburg (DE); Volker Landschutze, Berlin (DE); Jens Pilling, Köln (DE)

(73) Assignee: Bayer CropScience GmbH, Frankfurt (DE)

(*) Notice: Subject to any disclaimer, the term of this patent is extended or adjusted under 35 U.S.C. 154(b) by 0 days.

(21) Appl. No.: 10/038,224

(22) Filed: Oct. 19, 2001

(65) Prior Publication Data

US 2003/0110534 A1 Jun. 12, 2003

(30) Foreign Application Priority Data

Oct. 23, 2000 (DE) .......................................... 100 52 492
Dec. 22, 2000 (DE) .......................................... 100 64 805

(51) Int. Cl.$^7$ ........................ C12N 15/82; C12N 15/29; C12N 15/54; A01H 5/00; C12P 19/04
(52) U.S. Cl. ........................ 800/284; 800/278; 800/287; 800/320; 800/320.1; 800/320.2; 800/320.3; 435/69.1; 435/101; 435/194; 435/412; 435/419; 435/424
(58) Field of Search ................................. 800/278, 284, 800/287, 320, 320.1, 320.2, 320.3; 435/69.1, 101, 194, 412, 419, 424

(56) References Cited

U.S. PATENT DOCUMENTS 6,207,880 B1 * 3/2001 Kossmann et al. ......... 800/284

FOREIGN PATENT DOCUMENTS

| WO | WO 97/11188 | 3/1997 |
|----|-------------|--------|
| WO | WO 99/53072 | * 10/1999 |

OTHER PUBLICATIONS

Kossmann et al. Progress Biotechnol. 10:271–278, 1995.*
Ritte et al. Starch 52 (6–7):175–185, 2000.*
W. R. Morrison, "Starch Lipids and How They Relate to Starch Granule Structure and Functionality", *Osborne Medal Lecture*, Cereal Foods World, pp. 437–446.
Jane et al, "Phosphorus in Rice and Other Starches", Cereal Foods World, Nov.–Dec. 1996, vol. 41, No. 11, pp. 827–832.
Lim et al, "Characterization of Phosphorus in Starch by $^{31}$P–Nuclear Magnetic Resonance Spectroscopy", Cereal Chemistry, vol. 71, No. 5, 1994, pp. 489–193.
Lorberth et al, "Inhibition of a Starch–granule–bound protein leads to modified starch and repression of cold sweetening", Nature Biotechnology, vol. 16, May 1998, pp. 473–477, also referred to as XP 002111459.
Ritte et al, "Reversable binding on the starch–related R1 protein to the surface of transitory starch granules", The Plant Journal, 2000 21(4), pp. 387–391.
Jansen et al, "Analysis of cDNA clones encoding the entire precursor–polypeptide for ferredoxin: NADP oxidoreductase from spinach", Current Genetics, 1988, 13: pp. 517–522.
Klösgen et al, "The amyloplast–targeting transit peptide of the *waxy* protein of maize also mediates protein transport in vitro into chloroplasts", Mol. Gen Getics 1989, 217, pp. 155–161.
Nielsen et al, "Starch Phosphorylation in Potato Tubers Proceeds Concurrently with de Novo Biosynthesis of Starch", Plant Physiol. 1994, 105: pp. 111–117.
Jane et al, "Internal Structure of the potato starch granule revealed by chemical gelatinization", Carbohydrate Research, 247, 1993, pp. 279–290.
Gough et al, "Effect of Metal Cations on the Swelling and Gelatinization Behaviour of Large Wheat Starch Granules", pp. 123–130.
Leisy et al, "Expression of a Rice Glutelin promotor in transgenic tobacco", Plant Molecular Biology, 14, 1989, pp. 41–50.
Zheng et al, "5$^7$ distal and proximal *cis*–acting regulator elements are required for developmental control of a rice seed storage protein *glutelin* gene", The Plant Journal, 1993 4(2), pp. 357–366.
Yoshihara et al, "A45–bp proximal region containing AACA and GCN4 motif is sufficient to confer endosperm–specific expression of the rice storage protein glutelin gene, *GluA–3*", FEBS Letters 383, 1996, pp. 213–218.
Werr et al, "Structure of the sucrose synthase gene on chromosome 9 of *Zea mays* L.", The EMBO Journal vol. 4, 1985, pp. 1373–1380.

(List continued on next page.)

Primary Examiner—David T. Fox
(74) Attorney, Agent, or Firm—Frommer Lawrence & Haug LLP

(57) ABSTRACT

The present invention relates to monocotyledon plant cells and plants which are genetically modified, wherein the genetic modification consists of the introduction of an extraneous nucleic acid molecule which codes for a protein with the biological activity of an R1 protein. The present invention further relates to means and methods for the production thereof. Plant cells and plants of this type synthesise a modified starch, which is characterized in that it has an increased phosphate content and/or a modified phoshorylation pattern and/or an increased final viscosity in an RVA profile and/or a reduced peak temperature in DSC analysis and/or an increased gel strength in the texture analysis compared with starch from corresponding non-genetically modified monocotyledon plants. Therefore, the present invention also relates to the starch which is synthesized from the plant cells and plants according to the invention, and to methods of producing said starch. The present invention further relates to wheat flours which contain said modified starches, and to food products and bakery products which contain said wheat flours and/or starch.

17 Claims, 6 Drawing Sheets

OTHER PUBLICATIONS

Anderson et al, "Conservation in wheat high–molecular–weight glutenin gene promotor sequences: comparisons among loci and among alleles of the GLU–B1 locus", Theor. Appln. Genet, (1998), 96, pp. 568–576.

Thomas et al, "Identification of an Enhancer Element for the Endosperm–Specific Expression of High Molecular Weight Glutenin", The Plant Cell, vol. 2, pp. 1171–1180, Dec. 1990.

Sengupta–Gopalan et al, "Developmentally regulated expression of the bean β–phaseolin gene in tobacco seed", Proc. Natl. Acad. Sci. USA, vol. 82, pp. 3320–3324, May 1985.

Bustos et al, "Regulation of β–Glucuronidase Expression in Transgenic Tobacco Plants by an A/T–Rich, cis–Acting Sequence Found Upstream of a French Bean B–Phaseolin Gene", The Plant Cell, vol. 1, pp. 839–853, Sep. 1989.

Pedersen et al, "Cloning and Sequence Analysis Reveal Structural Variation among Related Zein Genes in Maize", Cell, vol. 29, pp. 1015–1026, Jul. 1982.

Quattrocchio et al, "The maize zein gene zE19 contains two distinct promotors which are independently activiated in endosperm and anthers of transgenic *Petunia* plants", Plant Molecular Biology, 15, pp. 81–93, 1990.

\* cited by examiner

MONOCOTYLEDON PLANT CELLS AND PLANTS WHICH SYNTHESISE MODIFIED STARCH

FIELD OF THE INVENTION

The present invention relates to monocotyledon plant cells and plants which are genetically modified, wherein the genetic modification consists of the introduction of an extraneous nucleic acid molecule which codes for a protein with the biological activity of an R1 protein. The present invention further relates to means and methods for the production thereof. Plant cells and plants of this type synthesise a modified starch which is characterised in that it has an increased phosphate content and/or a modified phosphorylation pattern and/or an increased final viscosity in an RVA profile and/or a reduced peak temperature in DSC analysis and/or an increased gel strength in the texture analysis compared with starch from corresponding non-genetically modified monocotyledon plants. Therefore, the present invention also relates to the starch which is synthesised from the plant cells and plants according to the invention, and to methods of producing said starch. The present invention further relates to wheat flours which contain said modified starches, and to food products and bakery products which contain said wheat flours and/or starch.

With regard to the increasing importance which has recently been attached to substances of plant content as renewable sources of raw materials, one of the tasks of biotechnological research is to endeavour to adapt these plant raw materials to the requirements of the industry which processes them. To facilitate the use of renewable raw materials in as many fields of use as possible, it is also necessary to provide a considerable multiplicity of substances.

Apart from oils, fats and proteins, polysaccharides constitute the important renewable raw materials from plants. In addition to cellulose, starch, which is one of the most important storage materials in higher plants, assumes a central position in polysaccharides.

Polysaccharide starch is a polymer of chemically uniform basic components, namely glucose molecules. However, it is a very complex mixture of different forms of molecules, which differ with regard to their degree of polymerisation and the occurrence of branched region in the glucose chains. Starch therefore does not constitute a uniform raw material. A distinction is made between two chemically different components of starch: amylose and amylopectin. In typical plants which are used for starch production, such as maize, wheat or potatoes, the synthesised starch consists of up to about 20%–30% of amylose starch and up to about 70%–80% of amylopectin starch.

Amylose was for a long time considered to be a linear polymer consisting of α-1,4-glycosidically bonded α-D-glucose monomers. In more recent studies, however, the presence of about 0.1% of α-1,6-glycosidic branching sites has been detected (Hizukuri and Takagi, Carbohydr. Res. 134, (1984), 1–10; Takeda et al., Carbohydr. Res. 132, (1984), 83–92). Basically, however, achieving a complete separation of amylose from amylopectin very difficult, so that the quality of the amylose is strongly dependent on the type of separation method selected. In contrast to amylose, amylopectin is more strongly branched and comprises about 4% of branching sites which are formed due to the occurrence of additional α-1,6-glycoside linkages. Amylopectin constitutes a complexes mixture of differently branched glucose chains. A further significant difference between these two molecules is their molecular weight. Whereas amylose, depending on the origin of the starch, has a molecular weight of $5 \times 10^5 – 10^6$ Da, that of amylopectin ranges between $10^7$ and $10^8$ Da. These two macromolecules can be by distinguished by their molecular weight and by their different physicochemical properties, which are most readily manifested by their different iodine bonding properties.

A further significant difference between amylose and amylopectin is the relative amounts of trace substances which can exist in association with these macromolecules. Amylose has a high affinity for hydrophobic molecules. In cereals in particular, amylose can be complexed with relatively high amounts of lipids (Morrison, Cereal Foods World 40, (1995), 437–446). On the other hand, amylopectin can contain covalently bonded inorganic phosphate in the form of starch phosphate monoesters, which has not hitherto been described for amylose. High contents of phosphate monoesters are found in particular in starches which are obtained from tubers. Amongst commercially available starches, potato starch has the highest phosphate content, which can range between 10–30 nmol $mg^{-1}$ starch. In some types of Curcuma the phosphate content can even be 2 to 4 times higher (Bay-Smidt et al., 5th ISPMP Meeting Proceedings, (1997), 741), whilst it is about 100 times less in cereals (Kasemsuwan and Jane, Cereal Chem. 73, (1996), 702–707). In contrast to starches from tubers, roots and legumes, the detectable phosphate in cereal starches (monocotyledon plants) rarely occurs in the form of starch monoester derivatives, but mainly occurs in the form of phospholipids (Jane et al., Cereal Foods World 41, (1996), 827–832).

Apart from its amylose/amylopectin ratio and phosphate content, the functional properties of starch are influenced by its molecular weight, its pattern of side chain distribution, its content of ions, its lipid and protein content, etc. Important functional properties which should be cited here are the solubility, the retrogradation behaviour, the water absorption capacity, the film-forming properties, the viscosity, the conglutination properties, the freeze-thaw stability, the stability in relation to acids, the gel strength, etc. The starch grain size can also be important for various applications.

In principle, the phosphate content can be modified either by genetic engineering approaches or by the subsequent chemical phoshorylation of native starches (see, for example: Starch Chemistry and Technology. Eds. R. L. Whistler, J. N. BeMiller and E. F. Paschall. Academic Press, New York, 1988, 349–364). Chemical modifications are generally costly and time-consuming, however, and result in starches, the physicochemical properties of which can differ from those of starches modified in vivo.

Since starches from monocotyledon wild-type plants, particularly from cereal plants (wheat, rice, maize, oats, millet, rye), only have a very low content of phosphate in the form of starch phosphate monoesters (Lim et al. Cereal Chem. 71, (1994), 488), one object of the present invention is to provide monocotyledon plants which synthesise starches with an increased phosphate content (content of starch phosphate monoesters) and modified physicochemical properties compared with corresponding wild-type plant cells and plants.

The underlying object of the present invention is thus to provide genetically modified monocotyledon plant cells and plants which synthesise starches with modified structural and/or functional properties compared with corresponding non-genetically modified wild-type plant cells and plants, and is also to provide starch, the structural and/or functional properties of which differ from those of starch from corresponding non-genetically modified wild-type plant cells and plants and from those of chemically modified starch, and which is thus more suitable for general and/or special industrial purposes of use.

This object is achieved by the provision of the embodiments described in the claims, because it has surprisingly been found that the introduction of an extraneous nucleic acid molecule into the genome of monocotyledon plant cells and plants results in a modification of the structural and/or functional properties of the starch which is synthesised in said monocotyledon plant cells and plants.

Expression of the extraneous nucleic acid molecule is primarily advantageous in starch-storing organs of monocotyledon plants, particularly of wheat plants, and leads to an increase of the phosphate content and modification of the viscosity properties of the starch which can be isolated from the starch-storing organs compared with starches which can be isolated from starch-storing organs of corresponding non-genetically modified wild-type plants, particularly wheat plants. Moreover, the starches according to the invention are distinguished from chemically phosphorylated starches by a modified phoshorylation pattern and modified viscosity properties, and after conglutination of the starches and gel formation are also distinguished by modified gel strengths.

SUMMARY OF THE INVENTION

Thus the present invention relates to monocotyledon genetically modified plant cells, wherein the genetic modification consists of the introduction of at least one extraneous nucleic acid molecule and the extraneous nucleic acid molecule is selected from the group consisting of:

a) nucleic acid molecules which comprise the coding region of the nucleotide sequence represented in Seq ID No. 1;

b) nucleic acid molecules which encode an R1 protein from Solanum tuberosum with the amino acid sequence given in Seq ID No. 2;

c) nucleic acid molecules which constitute a derivative of the nucleotide sequence given in Seq ID No. 1; and d) nucleic acid molecules which constitute fragments of the nucleic acid molecules cited in (a), (b) or (c).

In the sense of the present invention, the term "genetically modified" means that the genetic information of the plant cell is modified by the introduction of an extraneous nucleic acid molecule and that the presence or expression of the extraneous nucleic acid molecule results in a phenotypic modification. The term "phenotypic modification" preferably means a measurable modification of one or more functions of the cells. For example, the genetically modified plant cells according to the invention exhibit a modified expression pattern. In the sense of the present invention, the term "genetically modified" means that the monocotyledon plant cell according to the invention contains at least one extraneous nucleic acid molecule which is integrated in the genome in a stable manner.

In the sense of the present invention, the term "extraneous nucleic acid molecule" is to be understood to mean a nucleic acid molecule which codes for a protein with the biological activity of an R1 protein, preferably an R1 protein from Solanum tuberosum, and which does not occur naturally in corresponding non-genetically modified wild-type plant cells. The extraneous nucleic acid molecule is preferably a recombinant molecule which consists of different elements, the combination or specific spatial arrangement of which does not occur naturally in plant cells. The monocotyledon plant cells according to the invention contain at least one extraneous nucleic acid molecule, wherein the latter is preferably linked to regulatory DNA elements which ensure transcription in plant cells, particularly with a promoter. An example of an extraneous nucleic acid molecule which codes for an R1 protein from Solanum tuberosum is represented in SEQ ID No. 1. Nucleotide sequences which code for an R1 protein from Solanum tuberosum have also been described in WO 97/11188 A1 and by Lorberth et al. (Nature Biotech. 16, (1998), 473–477).

The important characteristics of of R1 proteins from Solanum tuberosum are i) their amino acid sequence (see SEQ ID No. 2, for example); ii) their location in the stroma of plastids of plant cells, wherein they can exist there both in a form bound to starch grains and in soluble form; and iii) their capacity for influencing the degree of phoshorylation of starch in plants. For example, inhibition of the R1 gene which codes for an R1 protein from potatoes in transgenic potato plants results in a reduction of the phosphate content of the starch which can be isolated from the potato tubers. Furthermore, Lorberth et al. showed that the R1 protein from Solanum tuberosum is capable of phosphorylating bacterial glycogen if the corresponding R1 cDNA is expressed in $E.$ $coli$ (Lorberth et al., Nature Biotech. 16, (1998), 473–477). Ritte et al. (Plant J. 21, (2000), 387–391) showed that the R1 protein from Solanum tuberosum binds reversibly to starch grains in potato plants, wherein the strength of binding to the starch grain depends on the metabolic status of the plant. In starch grain-bound form, the protein in potato plants mainly occurs in leaves which are kept in the dark. After the leaves are illuminated, however, the protein is mainly present in a soluble form which is not bound to starch grains.

Moreover, inhibiting the expression of the R1 gene from potatoes in transgenic potato plants results in a "starch-excess" phenotype, i.e. the leaves of corresponding plants have an increased content of starch (Lorberth et al., Nature Biotech. 16, (1998), 473–477). In addition, the tubers of such potato plants are distinguished in that after cold storage they exhibit reduced "cold-induced sweetening" (Lorberth et al., Nature Biotech. 16, (1998), 473–477).

In principle, the extraneous nucleic acid molecule which codes for an R1 protein can originate from any kind of potato or potato plant, preferably from potatoes of the Tomensa, Desiree, Tempora and Thomana varieties.

In one preferred embodiment, the extraneous nucleic acid molecule has the nucleotide sequence represented in SEQ ID No. 1.

In a further preferred embodiment the invention comprises the extraneous nucleic acid molecule of the coding region of the nucleotide sequence represented in SEQ ID No.1.

In a further preferred embodiment of the invention, the extraneous nucleic acid molecule encodes an R1 protein from Solanum tuberosum which has the amino acid sequence given in SEQ ID No. 2.

In yet another embodiment of the invention, the extraneous nucleic acid molecules comprise the coding region of the mature (without a plastidary signal peptide) protein (bp 447–bp 4607 of the nucleotide sequence given in SEQ ID No. 1). Instead of the plastidary N-terminal signal peptide of the R1 protein from potatoes (amino acids 1 to 77 coded by nucleotides 216 to 446 of the nucleotide sequence given in SEQ ID No.1), in this embodiment of the invention the extraneous nucleic acid molecules comprise a heterologous plastidary signal sequence, i.e. a signal sequence which does not exist naturally in association with the mature R1 protein. Plastidary signal sequences are known to one skilled in the art.

The signal sequence of Ferrodoxin:NADP⁺ oxidoreductase (FNR) from spinate can be used as a plastidary signal sequence, for example. This sequence contains the 5'-non-translated region as well as the flanking transit peptide sequence of the cDNA of the plastidary protein Ferrodoxin:NADP⁺ oxidoreductase from spinate (nucleotides −171 to +165; Jansen et al., Current Genetics 13, (1988), 517–522).

In addition, for example, the transit peptide of the waxy protein from maize plus the first 34 amino acids of the mature waxy protein can be used as a signal sequence (Klösgen et al., Mol. Gen. Genet. 217, (1989), 155–161). Furthermore, the transit peptide of the waxy protein from maize can be used without the first 34 amino acids of the mature waxy protein.

In a further preferred embodiment of the invention, the extraneous nucleic acid molecule constitutes a derivative of the nucleotide sequence given in SEQ ID No.1.

In the sense of the present invention, the expression "derivative" means that the sequences of these molecules differ at one or more positions from the nucleotide sequence given in SEQ ID No. 1 and exhibit a high degree of homology with the coding region of the nucleotide sequence given in SEQ ID No. 1. In addition, derivatives are distinguished in that they code for a protein with the biological activity of an R1 protein, preferably of an R1 protein from Solanum tuberosum. In the sense of the present invention, "homology" means a sequence identity of nucleotide sequences of at least 65%, particularly of at least 85%, more particularly an identity of at least 90%, preferably more than 95% and most preferably more than 98%. Differences from the nucleic acid molecules described above can occur due to deletion, addition, substitution, insertion or recombination.

The degree of homology is preferably determined by comparing the sequence of the respective nucleotide sequence with the coding region of SEQ ID No.1, particularly with region of SEQ ID No.1 (bp447–bp4607) which codes for the mature protein of the nucleotide sequence given in SEQ ID No. 1). If the sequences to be compared are of different lengths, the degree of homology preferably refers to the percentage of nucleotides in the shorter nucleotide sequence which are identical to the nucleotides of the longer sequence, i.e. the sequence identity is determined for the region in which the respective nucleotide sequences overlap. Sequence comparisons can be made using known computer programs, such as the Clustal W program (Thompson et al., Nucleic Acids Research 22, (1994), 4673–4680), which is distributed by Julie Thompson and Toby Gibson European Molecular Biology Laboratory, Meyerhofstrasse 1, D 69117 Heidelberg, Germany). Clustal W can also be downloaded from various internet sites, e.g. that of the IGBMC (Institut de Génétique et de Biologie Moléculaire et Cellulaire, B.P.163, 67404 Illkirch Cedex, France; and that of the EBI (European Bioinformatics Institute), as well as from internet sites with links to the EBI (European Bioinformatics Institute, Wellcome Trust Genome Campus, Hinxton, Cambridge CB10 1SD, UK).

When using the ClustalW program (Version 1.8), the default values of the various parameters are employed. In the case of DNA sequence comparisons, these parameters have the following values: KTUPLE=2, TOPDIAGS=4, PAIRGAP=5, DNAMATRIX:IUB, GAPOPEN=10, GAPEXT=5, MAXDIV=40, TRANSITIONS: unweighted.

In the case of protein sequence comparisons the default values of the parameters of the ClustalW program are likewise used. These parameters have the following values: KTUPLE=1, TOPDIAG=5, WINDOW=5, PAIRGAP=3, GAPOPEN=10, GAPEXTEND=0.05, GAPDIST=8, MAXDIV=40, MATRIX=GONNET, ENDGAPS(OFF), NOPGAP, NOHGAP.

The degree of homology can be determined, for example, using known computer programs such as Mview Brown, N. P., Leroy C., Sander C. (1998). MView: A Web compatible database search or multiple alignment viewer. *Bioinformatics*, 4(4):380–381).

In the sense of the present invention, "homology" also means that there is functional and/or structural equivalence between the respective nucleic acid molecules or the proteins which they encode. The nucleic acid molecules which are homologous with the nucleic acid molecules described in SEQ ID No.1 and which constitute derivatives of these molecules are variations of these molecules which constitute modifications which perform the same biological function, and which in vivo are also capable of increasing the phosphate content of starches in monocotyledon plants. These can be either naturally occurring variations, for example sequences from other types of potatoes, or mutations, wherein said mutations may have been formed naturally or may have been introduced by targeted mutagenesis.

In a further embodiment of the invention, the derivative of SEQ ID No.1 comprises allelic variants of the nucleic acid molecule given in SEQ ID No.1. These allelic variants are naturally occurring variants which are capable of increasing the phosphate content of starches.

In a further embodiment of the invention, the extraneous nucleic acid molecule constitutes a fragment of the extraneous nucleic acid molecule which is defined according to the invention.

In the sense of the present invention, the term "fragment" denotes parts of the extraneous nucleic acid molecule which code for a biologically active, preferably enzymatically active, part of the R1 protein.

A biologically active part of an R1 protein is distinguished in that in planta it can cause an increase of the phosphate content with superexpression of the extraneous nucleic acid molecule and/or that after expression in *E. coli* it facilitates phoshorylation of glycogen (see WO 97/11188 A1, Example 9).

The proteins which are encoded by the different variants (fragments, derivatives, allelic variants) of the extraneous nucleic acid molecule exhibit defined general characteristics. Examples of the latter include the biological activity, the enzymatic activity, or a similar primary structure which can be investigated by means of the protein homology comparisons described above. The amino acid sequences of the proteins exhibit a mutual homology of at least 60%, preferably at least 85%, particularly at least 95% and most preferably at least 97%.

In addition to the characteristics described above, the extraneous nucleic acid molecules may be characterised in that they code for proteins with the biological activity of R1 proteins, which comprise at least one, preferably at least five, particularly at least 10 and most preferably all of the following characteristic peptide motifs:

DKAAET (SEQ ID No. 3), IADME (SEQ ID No. 4), VWMRFM (SEQ ID No. 5), MQEWHQ (SEQ ID No. 6), LGHYM (SEQ ID No. 7), ERGYEE (SEQ ID No.8), KAVLDR (SEQ ID No. 9), LSSLL (SEQ ID No. 10), IPDGAV (SEQ ID No.11), KVCFAT (SEQ ID No. 12), ISADEF (SEQ ID No. 13), PFGVFE (SEQ ID No. 14), SSGDD (SEQ ID No. 15), SFICKK (SEQ ID No. 16).

Amongst other differences, the plant cells according to the invention can also be distinguished from naturally occurring plant cells in that they contain an extraneous nucleic acid molecule which does not occur naturally in these cells, or that a molecule such as this is integrated at a place in the genome of the cell at which it does not occur naturally, i.e. in a different genomic environment. Moreover, transgenic plant cells of this type according to the invention can be distinguished from naturally occurring plant cells in that they contain at least one copy of the extraneous nucleic acid molecule which is integrated in a stable manner in their genome contain, optionally in addition to copies of a molecule such as this which occur naturally in the cells. If the nucleic acid molecules which are introduced into the cells are additional copies of molecules which already occur naturally in the cells, the plant cells according to the invention can be distinguished in particular from naturally occurring plant cells in that these additional copies are located at sites in the genome at which they do not occur naturally. This can be detected subsequently by means of Southern blotting analysis, for example.

Furthermore, the plant cells according to the invention are preferably distinguished from naturally occurring plant cells by at least one of the following features: if the nucleic acid molecule which is introduced is heterologous with respect to the plant the transgenic plant cells according to the invention comprise transcripts of the nucleic acid molecules which are introduced, in fact even in those organs in which no transcripts can be detected in wild-type plants. Plant cells according to the invention preferably contain transcripts of the extraneous nucleic acid molecules. These can be detected by Northern blotting analysis, for example. Plant cells according to the invention preferably contain a protein which is encoded by an introduced extraneous nucleic acid molecule. This additional protein can be detected by immunological methods for example, particularly by Western blotting analysis.

In one preferred embodiment, the plant cells and plants according to the invention exhibit an increased biological activity of the R1 protein compared with corresponding non-genetically modified wild-type plant cells and wild-type-plants. In connection with the present invention, an "increased biological activity of the R1 protein" can be determined, for example, by measuring the phosphate content of the starches which are synthesised in the plant cells and plants according to the invention. Compared with starches from corresponding non-genetically modified wild-type plant cells, starches from the plant cells according to the invention, which exhibit increased biological activity of the R1 protein, are distinguished in that they synthesise a starch with an increased phosphate content, preferably an increased phosphate content in the C6 position of the glucose monomer.

Moreover, an increased biological activity of the R1 protein can be determined by measuring the amount of R1-transcripts, e.g. by Northern blotting analysis, compared with the amount of R1-transcripts of corresponding non-genetically modified wild-type plants.

Furthermore, an increased biological activity of the R1 protein can be determined by measuring the amount of R1 protein, e.g. by Western blotting analysis, compared with the amount of R1 protein of corresponding non-genetically modified wild-type plants.

It has been found that the monocotyledon plant cells according to the invention synthesise a starch with an increased phosphate content in the C6 position of the glucose monomer and/or a modified phosphorylation pattern and/or modified viscosity properties compared with starch from corresponding non-genetically modified plant cells of wild-type-plants.

Therefore, the present invention preferably relates to plant cells according to the invention which synthesise a starch has an increased phosphate content in the C6 position of the glucose monomer and/or a modified phoshorylation pattern and/or modified viscosity properties compared with starch from corresponding non-genetically modified plant cells of wild-type-plants.

In the sense of the present invention, the term "phosphate content" denotes the content of phosphate which is covalently bonded in the form of starch phosphate monoesters.

In the sense of the present invention, the term "C6 position" is to be understood to mean phosphate groups, which are bonded to the glucose monomer of the starch at carbon atom position "6".

In connection with the present invention, the expression "increased phosphate content in the C6 position" is to be understood to mean that glucose monomer phosphate groups can be detected in the in the C6 position by means of an optical-enzymatic test (Nielsen et al., Plant Physiol. 105, (1994), 111–117, see methods).

The expression "increased phosphate content in the C6 position" is preferably understood to mean an increase in the phosphate content of the starch in the C6 position of the glucose monomer by at least 20%, preferably by at least 50% and most preferably by at least 100%, compared with the phosphate content of starch from corresponding non-genetically modified wild-type-plants.

In principle, the C2, C3 and C6 positions of the glucose units can be phosphorylated in the starch in vivo. In connection with the present invention, the phosphate content in the C6 position (=C6 P content) can be determined by a glucose-6-phosphate determination by means of an optical-enzymatic test (Nielsen et al., Plant Physiol. 105, (1994), 111–117) (see methods).

In the sense of the present invention, the term "modified phoshorylation pattern means that the total phosphate content of phosphate groups which are covalently bonded to the starch within the various layers of the starch grain is modified compared with chemically phosphorylated starches which are produced from starches from corresponding non-genetically modified plants. Chemically phosphorylated starches are distinguished by a phosphate gradient inside the starch grains, wherein the outer layers are generally more strongly phosphorylated than are the inner layers. In contrast to this, the starches according to the invention are distinguished in that the phosphate groups are distributed differently over the various layers of the starch grain, i.e. the starches according to the invention can be characterised in that they do not comprise the gradients from the outside to the inside which are typical of chemically phosphorylated starches.

Methods of investigating the phoshorylation pattern of starch are known to one skilled in the art (see Jane and Shen, Carbohydrate Research 247, (1993), 279–290; Gough and Pybus, Staerke 25, (1973), 123–130, for example). These methods are based on step-wise chemical conglutination of the various layers of the starch grains, in which the conglutinated layers of the starch grains are mechanically removed in steps. This shelling procedure is followed by a determination of the total phosphate content of the various starch grain layers by standard methods.

In the sense of the present invention, the term "chemically phosphorylated starch" is to be understood to mean a starch which is produced by the chemical phoshorylation of native starch from corresponding non-genetically modified plant cells and/or plants. In connection with the present invention, chemically phosphorylated starch is preferably distinguished by an amylose content which is comparable with the amylose content of the starches according to the invention. During the chemical phoshorylation of native starches, the phosphate content in the C6 position is adjusted by selecting suitable test conditions so that the phosphate content in the C6 position of the chemically phosphorylated starch is identical to and/or comparable with the phosphate content in the C6 position of the glucose monomer of the starches according to the invention.

In connection with the present invention, the term "modified viscosity properties" is to be understood in particular to mean an increase in the final viscosity in an RVA profile and/or a lowering of the peak temperature in DSC analysis.

In a further preferred embodiment, the plant cells according to the invention synthesise a starch which has an increased final viscosity compared with starch from corresponding non-genetically modified wild-type plants.

In connection with the present invention, the term "final viscosity" is to be understood to mean the viscosity which can be determined from a viscosity profile (see FIG. 1) and which is denoted there as "final viscosity=Fin". The viscosity profile can be obtained by means of a Rapid Visco Analyzer (RVA) (Newport Scientific Pty Ltd, Investment Support Group, Warriewood, NSW 2102, Australia). In the analysis of wheat starches, the viscosity profile is determined by the following procedure: 2.5 g starch (dry substance) are taken up in 25 ml $H_2O$ and used for analysis in a Rapid Visco Analyzer (Newport Scientific Pty Ltd., Investment Support Group, Warriewood NSW 2102, Australia). The instrument is operated according to the manufacturer's instructions. The complete temperature programme is illustrated schematically in FIG. 1. Performing an RVA analysis is described in detail below (see methods). In the sense of the present invention, the term "increased final viscosity" means that the final viscosity is increased by at least 10%, preferably by at least 30%, particularly by at least 50% and most preferably by at least 80% compared with starches from corresponding non-genetically modified wild-type plant cells, wherein the final viscosity can be increased by 1000% at most, preferably by 500% at most, particularly by 250% at most, compared with starches from corresponding non-genetically modified wild-type plant cells.

In a further preferred embodiment, the plant cells according to the invention synthesise a starch which has an identical or comparable phosphate content in the C6 position of the glucose monomer and/or a reduced peak temperature compared with starch from corresponding non-genetically modified wild-type plants and/or compared with chemically phosphorylated starches.

In the context of the present invention, the term "peak temperature" should be understood to mean the temperature Tp which can be determined by means of differential scanning calorimetry (DSC), which is known to one skilled in the art. The peak temperature is the temperature which can generally be assigned to the first peak maximum of the DSC curve. It can be determined, for example, using an instrument supplied by Perkin Elmer (instrument designation: DSC-7) using capsules of large volume, wherein the sample to be investigated comprises a ratio of starch to total water content of about 1:4 and measurements are made over a temperature range from 10° C. to 160° C. at a heating rate of 10° C./min (see Example 4).

The term "reduced peak temperature" Tp means that compared with starches from corresponding non-genetically modified wild-type plant cells the peak temperature Tp is reduced by at least 1.5° C., preferably by at least 2.5° C., particularly by at least 4° C. and most preferably by at least 6° C., and is reduced at most by 5° C., by 12° C. or by 9° C.

In a further preferred embodiment, the present invention relates to plant cells according to the invention which synthesise a starch which after conglutination forms a gel, which has an increased gel strength compared with a gel formed from starch from corresponding non-genetically modified wild-type plant cells.

In the sense of the present invention, the term "increased gel strength" is to be understood to mean an increase gel strength by at least 20%, particularly by at least 50%, preferably by at least 80% and most preferably by at least 100%, with the maximum reduction being 500% at most or 250% at most compared with the gel strength of starch from corresponding non-genetically modified wild-type plant cells. In connection with the present invention, the gel strength can be determined by means of a texture analyser under the conditions described below (see methods).

In a further embodiment of the invention, the increase in the phosphate content of the starches can relate to the amylopectin component of the starch.

Therefore, the present invention also relates to plant cells according to the invention which synthesise a starch, the amylopectin component of which is phosphorylated and the amylose component of which has a reduced total phosphate content compared with the amylose component of corresponding chemically phosphorylated starches with the same starch phosphate content in the C6 position of the glucose monomer.

Therefore, in contrast to chemically phosphorylated starches with the same phosphate content in the C6 position of the glucose monomer, the starches of the plant cells according to the invention are distinguished in that that the amylose component of the starch from the plant cells according to the invention has a reduced total phosphate content and/or a reduced phosphate content in the C6 position of the glucose monomer compared with the amylose component of chemically phosphorylated starch with the same phosphate content in the C6 position of the glucose monomer, which is produced from starch, which preferably has a comparable amylose content, from corresponding non-genetically modified plants.

In connection with the present invention, the term "total phosphate content" is to be understood to mean the content of phosphate which is covalently bound in the form of starch phosphate monoesters in the C2, C3 and C6 positions of the glucose units. According to the invention, the content of phosphorylated non-glucans, such as phospholipids; is not included under the term "total phosphate content". Phosphorylated non-glucans therefore have to be quantitatively separated before the determination of the total phosphate content.

Methods of separating phosphorylated non-glucans (e.g. phospholipids) from starch are known to one skilled in the art.

In the sense of the present invention, the term "reduced total phosphate content" is to be understood to mean a reduction of the total phosphate content by at least 5%, particularly by at least 20%, preferably by at least 50% and most preferably by at least 80%, compared with the total phosphate content of the amylose component of a chemically phosphorylated starch with the same C6 phosphate content which is produced from starch from corresponding non-genetically modified plants. Methods of determining of the total phosphate content are known to one skilled in the art and are described below (see methods).

In the sense of the present invention, the term "reduced phosphate content in the C6 position of the glucose monomer" should be understood to mean a reduction of the phosphate content in the C6 position of the glucose monomer of the amylose component by at least 10%, particularly by at least 20%, preferably by at least 50% and most preferably by at least 80% compared with the phosphate content in the C6 position of the glucose monomer of the amylose component of a chemically phosphorylated starch of the same C6 phosphate content which is produced from starch from corresponding non-genetically modified plants.

Methods of determining of the phosphate content in the C6 position of the glucose monomer are known to one skilled in the art and are described below (see methods).

In the sense of the present invention the term "amylopectin component" is to be understood to mean the amylopectin of the starch.

In the sense of the present invention, term "amylose component" is to be understood to mean the amylose of the starch.

Methods of separating amylose and amylopectin are known to one skilled in the art. For example, the amylose component can be obtained by aqueous leaching of the starch, as described, for example, by Roger & Colonna (International Journal of Biological Macromolecules 19, (1996), 51–61).

In a further preferred embodiment of the present invention, the starches according to the invention are additionally characterised in that the ratio of the C6 phosphate content of the glucose monomer in the C6 position of the amylose component to the C6 phosphate content of the glucose monomer in the C6 position of the starch is less than 0.75, particularly less than 0.5, preferably less than 0.25 and most preferably less than 0.20. In contrast to chemically phosphorylated starches, the starches according to the invention are distinguished in that the major part of the phosphate in the C6 position of the glucose monomer is detected in the amylopectin component of the starch and not in the amylose component.

The plant cells according to the invention originate from monocotyledon plants. They are preferably plant cells from plants which are used in agriculture, i.e. from plants, which are cultivated by humans for the purpose of nourishment or for technical purposes, particularly industrial purposes. Thus the present invention preferably relates to plant cells from starch-synthesising or starch-storing plants, e.g. rye, barley, oats, wheat, millet, rice or maize.

In one preferred embodiment of the present invention, the plant cells according to the invention originate from a plant of the group consisting of wheat, rice, barley, oats, rye and maize. Plant cells from wheat, rice and maize plants are preferred; plant cells from wheat plants are particularly preferred.

In one particularly preferred embodiment, the plant cells according to the invention synthesise a starch which in the C6 position of the glucose monomer has a phosphate content of at least 0.1 nmol C6 P mg$^{-1}$ starch, particularly at least 0.5 nmol C6 P mg$^{-1}$, preferably at least 1 nmol C6 P mg$^{-1}$ starch, more preferably at least 2 nmol C6 P mg$^{-1}$ starch, most preferably at least 5 nmol C6 P mg$^{-1}$ starch, most particularly preferably at least 10 nmol C6 P mg$^{-1}$, starch, wherein the plant cells according to the invention synthesise a starch which in the C6 position of the glucose monomer has a phosphate content of 100 nmol C6 P mg$^{-1}$ starch at most, particularly 50 nmol C6 P mg$^{-1}$ starch at most, and most particularly 25 nmol C6 P mg$^{-1}$ starch at most.

In a further embodiment of the invention, the plant cells according to the invention can synthesise a starch which in the C6 position of the glucose monomer has a phosphate content of at least 15 nmol C6 P mg$^{-1}$ starch, wherein the plant cells according to the invention synthesise a starch which in the C6 position of the glucose monomer have a phosphate content of 100 nmol C6 P mg$^{-1}$ starch at most, particularly 50 nmol C6 P mg$^{-1}$ starch at most, and most particularly 25 nmol C6 P mg$^{-1}$ starch at most.

In a further embodiment, the present invention relates to a method of producing a plant cell according to the invention, wherein a cell of a monocotyledon plant is genetically modified, and wherein the genetic modification consists of the introduction of at least one extraneous nucleic acid molecule.

There is a multiplicity of techniques which are available for the transfer of DNA into a plant host cell. These techniques include the transformation of plant cells with T-DNA using *Agrobacterium tumefaciens* or *Agrobacterium rhizogenes* as a transformation agent, fusion of protoplasts, injection, electroporation of DNA, the introduction of DNA by means of biolistic techniques and other possible techniques. The use of the transformation of plant cells facilitated by agrobacteria has been intensively investigated and is satisfactorily described in EP 120516; Hoekema, Ind.: The Binary Plant Vector System Offsetdrukkerij Kanters B. V., Alblasserdam (1985), Chapter V; Fraley et al., Crit. Rev. Plant Sci. 4, 1–46 and An et al. EMBO J. 4, (1985), 277–287. For the transformation of potatoes, see Rocha-Sosa et al., EMBO J. 8, (1989), 29–33), for example.

The transformation of monocotyledon plants has in the meantime been routinely accomplished by means of a biolistic technique and by means of agrobacteria (Komari et al., (1998), Advances in cereal gene transfer; Current Opinion in Plant Biotechnology 1, page 161 et seq.; Bilang et al. (1999), Transformation of Cereals, Genetic Engineering, 12, pages 113–148, edited by: J K Setlow, Kluwer Academic/Plenum Publisher, New York). Vectors based on agrobacteria have been described (Chan et al., Plant Mol. Biol. 22, (1993), 491–506; Hiei et al., Plant J. 6, (1994) 271–282; Deng et al, Science in China 33, (1990), 28–34; Wilmink et al., Plant Cell Reports 11, (1992), 76–80; May et al., Bio/Technology 13, (1995), 486–492; Conner and Domisse, Int. J. Plant Sci. 153 (1992), 550–555; Ritchie et al, Transgenic Res. 2, (1993), 252–265). Alternative systems for the transformation of monocotyledon plants include transformation by means of a biolistic technique (Wan and Lemaux, Plant Physiol. 104, (1994), 37–48; Vasil et al., Bio/Technology 11 (1993), 1553–1558; Ritala et al., Plant Mol. Biol. 24, (1994), 317–325; Spencer et al., Theor. Appl. Genet. 79, (1990), 625–631), protoplast transformation, electroporation of partially permeabilised cells, and the introduction of DNA by means of glass fibres. In particular, the transformation of maize has been described many times in the literature (see WO 95/06128, EP 0513849, EO 0465875, EP 292435; Fromm et al., Biotechnology 8, (1990), 833–844; Gordon-Kamm et al., Plant Cell 2, (1990), 603–618; Koziel et al., Biotechnology 11 (1993), 194–200; Moroc et al., Theor. Appl. Genet. 80, (1990), 721–726, for example).

The successful transformation of other types of cereals has also been described, e.g. for barley (Wan and Lemaux, see above; Ritala et al., see above; Krens et al., Nature 296, (1982), 72–74) and for wheat (Becker et al., Plant J. 5 (2), (1994), 229–307; Nehra et al., Plant J. 5, (1994), 285–297).

Various transformation methods have been described for rice, e.g. transformation facilitated by agrobacteria (Hiei et al., Plant J. 6 (1994), 271–282; Hiei et al., Plant Mol. Biol.

35 (1997), 205–218; Park et al., J. Plant Biol. 38 (1995), 365–371), protoplast transformation (Datta, In "Gene transfer to plants", Potrykus, Spangenberg (Eds.), Springer-Verlag, Berlin, Heidelberg, 1995, 66–75; Datta et al., Plant Mol. Biol. 20 (1992), 619–629; Sadasivam et al., Plant Cell Rep. 13 (1994), 394–396), a biolistic technique for plant transformation (Li et al., Plant Cell Rep. 12 (1993), 250–255; Cao et al., Plant Cell Rep. 11 (1992), 586–591; Christou, Plant Mol. Biol. (1997), 197–203), and electroporation (Xu et al., In "Gene transfer to plants", Potrykus, Spangenberg (Eds.), Springer-Verlag, Berlin, Heidelberg, 1995, 201–208).

The present invention further relates to plants containing the plant cells according to the invention and/or which can be produced by regeneration from plant cells according to the invention. These plants are preferably useful monocotyledon plants, e.g. rye, barley, oats, wheat, millet, rice and maize. Wheat, rice and maize are preferred; wheat is particularly preferred.

The plants according to the invention synthesise a modified starch, the phosphate content of which and/or the phosphorylation pattern of which and/or the viscosity properties of which differ from those of starches from corresponding non-genetically modified wild-type-plants, as described in connection with the plant cells according to the invention.

Therefore, the present invention also relates to plants according to the invention which synthesise a starch, which has an increased phosphate content in the C6 position of the glucose monomer and/or exhibits a modified phoshorylation pattern and/or modified viscosity properties compared with starch from corresponding non-genetically modified plants.

The statements made in connection with the plant cells according to the invention are applicable with regard to the increase of the phosphate content in the C6 position of the glucose monomer of the starch, the modification of the phoshorylation pattern and the modification of the viscosity properties of the starch. The present invention preferably relates to plants according to the invention which synthesise a starch after conglutination forms a gel, which has an increased gel strength compared with a gel formed from starch from corresponding non-genetically modified wild-type-plants.

The term "increased gel strength" was defined in connection with the plant cells according to the invention.

In a further preferred embodiment of the invention, the plants according to the invention, preferably wheat plants, synthesise a starch, preferably wheat starch, which in the C6 position of the glucose monomer has a phosphate content of at least 0.1 nmol C6 P mg$^{-1}$ starch, particularly at least 0.5 nmol C6 P mg$^{-1}$, preferably at least 1 nmol C6 P mg$^{-1}$ starch, most preferably at least 2 nmol C6 P mg$^{-1}$ starch, particularly at least 5 nmol C6 P mg$^{-1}$ starch, quite most preferably at least 10 nmol C6 P mg$^{-1}$ starch, wherein the plants according to the invention synthesise a starch which in the C6 position of the glucose monomer has a phosphate content of 100 nmol C6 P mg$^{-1}$ starch at most, particularly 50 nmol C6 P mg$^{-1}$, starch at most, or 25 nmol C6 P mg$^{-1}$ starch at most.

In a further embodiment of the invention, the plants according to the invention can synthesise a starch which in the in the C6 position of the glucose monomer has a phosphate content of at least 15 nmol C6 P mg$^{-1}$ starch, wherein the plants according to the invention synthesise a starch which in the C6 position of the glucose monomer has a phosphate content of 100 nmol C6 P mg$^{-1}$ starch at most, particularly 50 nmol C6 P mg$^{-1}$ starch at most or 25 nmol C6 P mg$^{-1}$ starch at most.

In a further preferred embodiment of the invention, the plants according to the invention synthesise the starch according to the invention in the starch-storing organs of the plant according to the invention.

In a most preferred embodiment, the plants according to the invention synthesises a starch in its starch-storing organs which has an increased phosphate content in the C6 position of the glucose monomer and/or a modified phoshorylation pattern and/or modified viscosity properties compared with starch from starch-storing organs of corresponding non-genetically modified wild-type plants.

In this connection, the expression "starch-storing organs" is to be understood to mean those organs, e.g. the grains of maize, rice and wheat plants, which incorporate stored starch, in contrast to those organs, such as leaves, which only synthesise starch transiently.

Expression of the extraneous nucleic acid molecule is particularly advantageous in starch-storing organs of monocotyledon plants, especially in wheat plants, and results in an increase of the phosphate content of the starches which can be isolated from the starch-storing organs compared with starches which can be isolated from the starch-storing organs of corresponding non-genetically modified wild-type plants, particularly wheat plants.

Expression of the extraneous nucleic acid molecule in starch-storing organs of monocotyledon plants can be achieved firstly by the use of constitutive promoters, e.g. the promoter of the 35S RNA of the cauliflower mosaic virus (see U.S. Pat. No. 5,352,605, for example) and the ubiquitin promoter of maize (see U.S. Pat. No. 5,614,399, for example).

Promoters are preferably used which are specific for starch-storing organs, e.g. endosperm-specific promoters, such as the glutelin promoter (Leisy et al., Plant Mol. Biol. 14, (1990), 41–50; Zheng et al., Plant J. 4, (1993), 357–366; Yoshihara et al., FEBS Lett. 383, (1996), 213–218), the shrunken-1 promoter (Werr et al., EMBO J. 4, (1985), 1373–1380), the HMW promoter of wheat (Anderson, Theoretical and Applied Genetics 96, (1998), 568–576, Thomas, Plant Cell 2 (12), (1990), 1171–1180), the USP promoter, the phaseolin promoter (Sengupta-Gopalan, Proc. Natl. Acad. Sci. USA 82 (1985), 3320–3324, Bustos, Plant Cell 1 (9) (1989), 839–853) or promoters of zein genes from maize (Pedersen et al., Cell 29, (1982), 1015–1026; Quatroccio et al., Plant Mol. Biol. 15 (1990), 81–93) or caryopsis-specific promoters of GBSSI (granule bound starch synthase I) (DE10041861.9) and of SSII (soluble starch synthase II) from wheat (DE10032379.0).

In one particularly preferred embodiment, the plants according to the invention exhibit R1 gene expression in the starch-storing organs of said plants.

R1 gene expression can be determined, for example, by measuring the amount of R1 transcripts, e.g. by Northern blotting analysis, compared with the amount of R1 transcripts of wild-type plants.

Moreover, in connection with the present invention, R1 gene expression can be determined by measuring the amount of R1 protein, e.g. by Western blotting analysis. The amount of R1 protein is preferably determined by means of protein extracts which are isolated from plant cells of endosperm.

In a further embodiment of the invention, the plants according to the invention exhibit R1 gene expression in the starch-storing organs of said plants, which is increased compared with R1 gene expression in starch-storing organs of corresponding non-genetically modified wild-type-plants, preferably by at least 50%, most preferably by at least 100%, particularly by at least 250% and most particularly by at least 500%.

In one most preferred embodiment, the plants according to the invention exhibit a organ-specific expression of the extraneous nucleic acid molecule in the starch-storing organs of the plants according to the invention.

In the sense of the present invention, the term "organ-specific" is to be understood to mean that the selected promoter favours expression of the extraneous nucleic acid molecule in the starch-storing organs compared with mature leaves, and results in significantly increased degree of expression, such as a level of expression which is increased at least 2- to 5 times, preferably 5- to 10 times, most preferably 10- to 100 times.

In this embodiment of the invention, the plants according to the invention are distinguished in that due to the organ-specific expression of the extraneous nucleic acid molecule they exhibit increased R1 gene expression in the starch-storing organs compared with the gene expression of the endogeneous R1 gene in the starch-storing organs of a corresponding non-genetically modified wild-type-plant. In this embodiment of the invention, an increase in R1 gene expression in the leaves of the plants according to the invention cannot be detected to the same extent as that in the starch-storing organs. The increase in R1 gene expression is preferably related solely to the starch-storing organs.

In a preferred embodiment of the invention, the plants according to the invention are plants from the group consisting of wheat, rice, barley, millet, oats, rye and maize. Wheat, rice and maize plants are preferred; wheat plants are particularly preferred.

The invention also relates to a method of producing a plant as defined according to the invention, wherein (a) a cell of a monocotyledon plant is genetically modified, wherein the genetic modification consists of the introduction of at least one extraneous nucleic acid molecule;

(b) a plant is regenerated from the cell according to step (a); and optionally (c) further plants are produced from the plant produced according to step (b).

The present invention further relates to a method of producing a plant as defined according to the invention, which in the starch-storing organs of said plant synthesises a starch with an increased phosphate content and/or a modified phoshorylation pattern and/or an increased final viscosity and/or a reduced peak temperature compared with starch from starch-storing organs of wild-type-plants, wherein (a) a cell of a monocotyledon plant is genetically modified, wherein the genetic modification consists of the introduction of at least one extraneous nucleic acid molecule as defined according to the invention;

(b) a plant is regenerated from the cell according to step (a); and optionally (c) further plants are produced from the plant produced according to step (b).

The same applies to the genetic modification which is introduced according to step (a) as that which has already been explained above in connection with the plant cells and plants according to the invention.

The regeneration of plants according to step (b) can be accomplished by methods known to one skilled in the art.

The production of further plants according to step (c) of the method according to the invention can be accomplished, for example, by vegetative propagation ) e.g. via cuttings, tubers or via callus cultivation and the regeneration of whole plants) or by sexual propagation. Sexual propagation preferably occurs in a controlled manner, i.e. selected plants with defined properties are crossed and propagated with each other.

In one preferred embodiment of the invention, the methods according to the invention are distinguished in that the extraneous nucleic acid molecule which is introduced into, the plant cell according to step (a) is selected from the group consisting of:

(i) nucleic acid molecules which comprise the coding region of the nucleotide sequence represented in Seq ID No. 1;

(ii) nucleic acid molecules which encode an R1 protein from Solanum tuberosum with the amino acid sequence given in Seq ID No. 2;

(iii) nucleic acid molecules which constitute a derivative of the nucleotide sequence given in Seq ID No. 1; and (iv) nucleic acid molecules which constitute fragments of the nucleic acid molecules cited in (i), (ii) or (iii).

In one particularly preferred embodiment, the methods according to the invention are distinguished in that the extraneous nucleic acid molecule is under the control of a promoter, preferably an endosperm-specific and/or caryopsis-specific promoter, which organ-specifically facilitates R1 gene expression in starch-storing tissue.

Promoters of this type, such as endosperm-specific and caryopsis-specific promoters, have been exemplified above in connection with the plants according to the invention.

In a further embodiment, the methods according to the invention relate to useful monocotyledon plants, e.g. rye, barley, oats, wheat, millet, rice and maize. Wheat, rice and maize are preferred; wheat is particularly preferred.

The present invention also relates to the plants which can be obtained by the method according to the invention.

The present invention also relates to propagation material for plants containing plant cells according to the invention, and to the plants produced by the method according to the invention. In the sense of the present invention, the term "propagation material" comprises any constituents of the plant which are suitable for production or propagation by a vegetative or generative route. Cuttings, callus cultures, rhizomes or tubers are suitable for vegetative propagation, for example. Other propagation material comprises fruit, seeds, seedlings, protoplasts, cell cultures etc., for example. Seeds are the preferred propagation material.

In one preferred embodiment, the present invention relates to maize grains.

In a most preferred embodiment, the present invention relates to wheat grains.

The maize and wheat grains according to the invention are particularly suitable for the production of fodder and of food products.

The present invention further relates to the use of extraneous nucleic acid molecules as defined according to the invention for the production of plants according to the invention, preferably of wheat, maize and rice plants, most preferably wheat plants, or for the production of monocotyledon plant cells according to the invention.

The plant cells and plant according to the invention synthesise, particularly in their starch-storing organs, a starch, the physicochemical properties of which, particularly the phosphate content of and/or the viscosity behaviour of which and/or the phoshorylation pattern of which is modified compared with that of starch synthesised in wild-type-plants and compared with chemically phosphorylated starches.

Therefore, the present invention also relates to starch which can be obtained from the plant cells, plants and/or propagation material according to the invention.

In one preferred embodiment of the invention, the starches according to the invention are characterised in that they have an increased phosphate content in the C6 position of the glucose monomer and/or a modified phoshorylation pattern and/or an increased final viscosity and/or a reduced peak temperature compared with starch from corresponding non-genetically modified wild-type plants.

The present invention also relates starch which is characterised in that it has an increased phosphate content in the C6 position of the glucose monomer and/or a modified phoshorylation pattern and/or an increased final viscosity and/or a reduced peak temperature compared with starch from corresponding non-genetically modified wild-type plants.

The statements made in connection with the plant cells according to the invention are applicable with regard to the increase of the phosphate content in the C6 position, the modification of the phoshorylation pattern and the modification of the viscosity properties (final viscosity, peak temperature).

In a further embodiment, the invention relates to starches, preferably wheat starches, which are characterised in that in the C6 position of the glucose monomer they have a phosphate content of at least 0.1 nmol C6 P mg$^{-1}$ starch, particularly at least 0.5 nmol C6 P mg$^{-1}$ starch, preferably at least 1 nmol C6 P mg$^{-1}$ starch, most preferably at least 2 nmol C6 P mg$^{-1}$ starch, most particularly at least 5 nmol C6 P mg$^{-1}$ starch, quite most preferably at least 10 nmol C6 P mg$^{-1}$ starch and/or an increased final viscosity and/or a reduced peak temperature, wherein in the C6 position of the glucose monomer the starch according to the invention has a phosphate content of 100 nmol C6 P mg$^{-1}$ starch at most, particularly 50 nmol C6 P mg$^{-1}$ starch at most, or 25 nmol C6 P mg$^{-1}$ starch at most.

In a further embodiment of the invention, the starches according to the invention can be characterised in that in the C6 position of the glucose monomer they have a phosphate content of at least 15 nmol C6 P mg$^{-1}$ starch, wherein in the C6 position of the glucose monomer the starch according to the invention has a phosphate content of 100 nmol C6 P mg$^{-1}$ starch at most, particularly 50 nmol C6 P mg$^{-1}$ starch at most, or 25 nmol C6 P mg$^{-1}$ starch at most.

In a further preferred embodiment, the starches according to the invention, preferably wheat starches, are characterised in that after conglutination the starches according to the invention form gels which exhibit an increased gel strength compared with gels of corresponding chemically phosphorylated starches of the same phosphate content and/or compared with gels of starches from corresponding non-genetically modified plants.

In a further preferred embodiment of the invention, the starches according to the invention can be characterised in that the major part of the phosphate groups are bonded to the amylopectin component of the starch, whilst the amylose only has a very low content of covalently bonded starch monophosphate esters. Compared with chemically phosphorylated starches of comparable C-6 phosphate content, the starches according to the invention from the plant cells according to the invention are distinguished in that the amylose of the starches according to the invention is less strongly phosphorylated than is the amylopectin component.

In a further embodiment of the invention, the starches according to the invention can be characterised in that the amylose component of said starch has a reduced total phosphate content in the amylose component compared with the amylose component of chemically phosphorylated starch, which preferably has the same phosphate content in the C6 position of the glucose monomer.

Methods of determining of the total phosphate content are known to one skilled in the art and are described below (see methods).

In a further embodiment the invention, the starch according to the invention can be characterised in that the total phosphate content, which can be detected by 31P NMR (Kasemsuwan and Jane (Cereal Chemistry 73 (6), (1996), 702–707) of the amylose component of said starch is reduced by at least 5%, preferably by at least 20%, particularly by at least 50% and most preferably by at least 80%, compared with the amylose component of chemically phosphorylated starch with the same phosphate content in the C6 position of the glucose monomer which is produced from starch of corresponding non-genetically modified plants.

In one preferred embodiment of the invention, the starches according to the invention can be characterised in that they exhibit a modified phoshorylation pattern compared with chemically phosphorylated starches.

The term "modified phoshorylation pattern" has already been defined in connection with the plant cells according to the invention.

In one preferred embodiment of the invention, the starches are starches from useful monocotyledon plants, such as rye-, barley, oats, wheat, millet, rice and maize starch. Wheat, rice and maize starch are preferred; wheat starch is particularly preferred.

The present invention further relates to a method of producing the starch according to the invention, comprising the steps of extracting the starch from a plant or plant cell as described above and/or from starch-storing parts of plant such as this and/or from the propagation material according to the invention. A method such as this also preferably comprises the step of harvesting the cultivated plants and/or starch-storing parts of said plants before the extraction of the starch, and most preferably further comprises the step of cultivating plants according to the invention and/or of propagation materials according to the invention before harvesting. Methods of extracting starch from plants or from starch-storing parts of plants are known to one skilled in the art. Methods of extracting starch from various starch-storing plants are also described, for example, in "Starch: Chemistry and Technology (edited by: Whistler, BeMiller and Paschall (1994), 2$^{nd}$ Edition, Academic Press Inc. London Ltd; ISBN 0–12–746270–8; see Chapter XII, pages 412–468, for example: Maize and sorghum starches: production; by Watson; Chapter XIII, pages 469–479: Tapioca, arrowroot and sago starches: production; by Corbishley and Miller; Chapter XIV, pages 479–490: Potato starch: production and uses; by Mitch; Chapter XV, pages 491 to 506: Wheat starch: production, modification and uses; by Knight and Oson; and Chapter XVI, pages 507 to 528: Rice starch: production and uses; by Rohmer and Klem; and see Maize starch: Eckhoff et al., Cereal Chem. 73 (1996) 54–57. The extraction of maize starch on an industrial scale is generally effected by what is termed "wet milling"). Apparatuses which are customarily used for methods of extracting starch from plant material include mills, separators, decanters, hydrocyclones, spray driers and fluidised-bed driers.

The present invention also relates to starch according to the invention which can be obtained by the methods according to the invention which were described above. The starches according to the invention can be subsequently modified by methods known to one skilled in the art, and in their unmodified or modified form are suitable for various uses in the food or non-food sectors.

Therefore, the present invention also relates to starches as defined according to the invention which have been subsequently chemically and/or physically modified.

Various options which can be used for chemical and/or physical modification are described in detail below.

The production of modified starches by means of genetic engineering operations on a plant can firstly modify the properties of the starch obtained from the plant so that further modification by means of chemical or physical methods no longer appear to be necessary. Secondly, starches which have been modified by genetic engineering methods can be subjected to further chemical and/or physical modifications, which results in additional improvements in quality for some of the areas of use described above. These chemical and physical modifications are known in principle. In particular, they comprise modifications by means of:

heat treatment, treatment with acids, production of starch ethers, starch alkyl ethers, O-allyl ethers, hydroxylalkyl ethers, O-carboxylmethyl ethers, N-containing starch ethers, P containing starch ethers, S-containing starch ethers, production of crosslinked starches, production of starch graft polymers, oxidation, and esterification operations which are used for the production of phosphate, nitrate, sulphate, xanthate, acetate and citrate starches. Other organic acids can also be used for esterification.

In a further embodiment, the present invention relates to the use of the starches according to the invention in industry, preferably for the production of foodstuffs.

In a further embodiment, the invention relates to wheat flour which contains the starches according to the invention. Amongst its other properties, the wheat flour according to the invention is distinguished by modified baking properties compared with conventional wheat flours. Methods of producing wheat flour from wheat grains are known to one skilled in the art. By means of these methods, the wheat flour according to the invention can be isolated from the plant cells and plants according to the invention and from the propagation material according to the invention.

Thus the present invention also relates to wheat flour which can be obtained from the plant cells and plants according to the invention and from the propagation material according to the invention.

Compared with flours from corresponding non-genetically modified wild-type plants, the flours according to the invention are distinguished in particular by their enhanced water absorption capacity. Methods of determining water absorption capacity are known to one skilled in the art and are described in detail below (see methods).

In one preferred embodiment of the invention, the wheat flours exhibit a water absorption capacity which is increased by at least 5%, particularly by at least 15%, preferably by at least 20% and most preferably by at least 25% compared with wheat flours from corresponding non-genetically modified wheat plants.

Due to their high water absorption capacity, the flours according to the invention have the advantage for the industrial production of dough that less water has to be supplied to the flour during the dough preparation stage.

In a further embodiment, the present invention relates to the use of the wheat flour according to the invention and/or of the starch according to the invention for the production of a baking mixture and/or for the production of a food product.

In a further embodiment, the present invention relates the use of the wheat flour according to the invention and/or of the starch according to the invention for the coating of packages.

In a particularly preferred embodiment, the present invention relates to a baking mixture which contains the wheat flour according to the invention and/or the starch according to the invention. In this connection, the term "baking mixture" is to be understood to mean any mixture which can be used for the production of dough (e.g. yeast dough, pasta dough, shortcrust pastry, sour dough etc.) and/or of bakery products (e.g. bread, cakes, rolls, croissants, etc.).

In a further particularly preferred embodiment, the present invention relates to a food product, preferably bakery and dough products (e.g. pasta) which is produced using the wheat flour according to the invention and/or the baking mixture according to the invention and/or the starch according to the invention.

Compared with bakery products which are produced from wheat flours from corresponding non-genetically modified wheat wild-type wheat plants, the bakery products and/or food products according to the invention are distinguished on storage by a slowing down of the ageing process which the bakery products undergo.

The ageing process of a bakery product is closely linked to the degree of retrogradation (recrystallisation) of the amylopectin component of the starch. It is assumed that the ageing process of a bakery product and/or food product has progressed further, the higher is the degree of retrogradation of the amylopectin component The enthalpies of fusion of the amylopectin which can be determined by DSC provide information on the degree of retrogradation of the amylopectin. The degree of ageing of a bakery product can thus be determined by determining the enthalpy of fusion of the amylopectin at a given point in time by means of DSC (=differential scanning calorimetry) analysis (see methods).

If the enthalpy of fusion of the amylopectin of the bakery products and/or food products according to the invention is determined after storage for three and/or seven and/or thirteen days, for example, it is found that the enthalpy of fusion of the amylopectin is reduced compared with the enthalpy of fusion of the amylopectin of bakery products and/or food products which are stored for the same length of time and which are based on wheat flours of corresponding non-genetically modified wild-type plants. This shows that the bakery products and food products according to the invention are distinguished by a slower ageing process compared with conventional products.

DETAILED DESCRIPTION OF THE INVENTION

Methods

Figure 1:
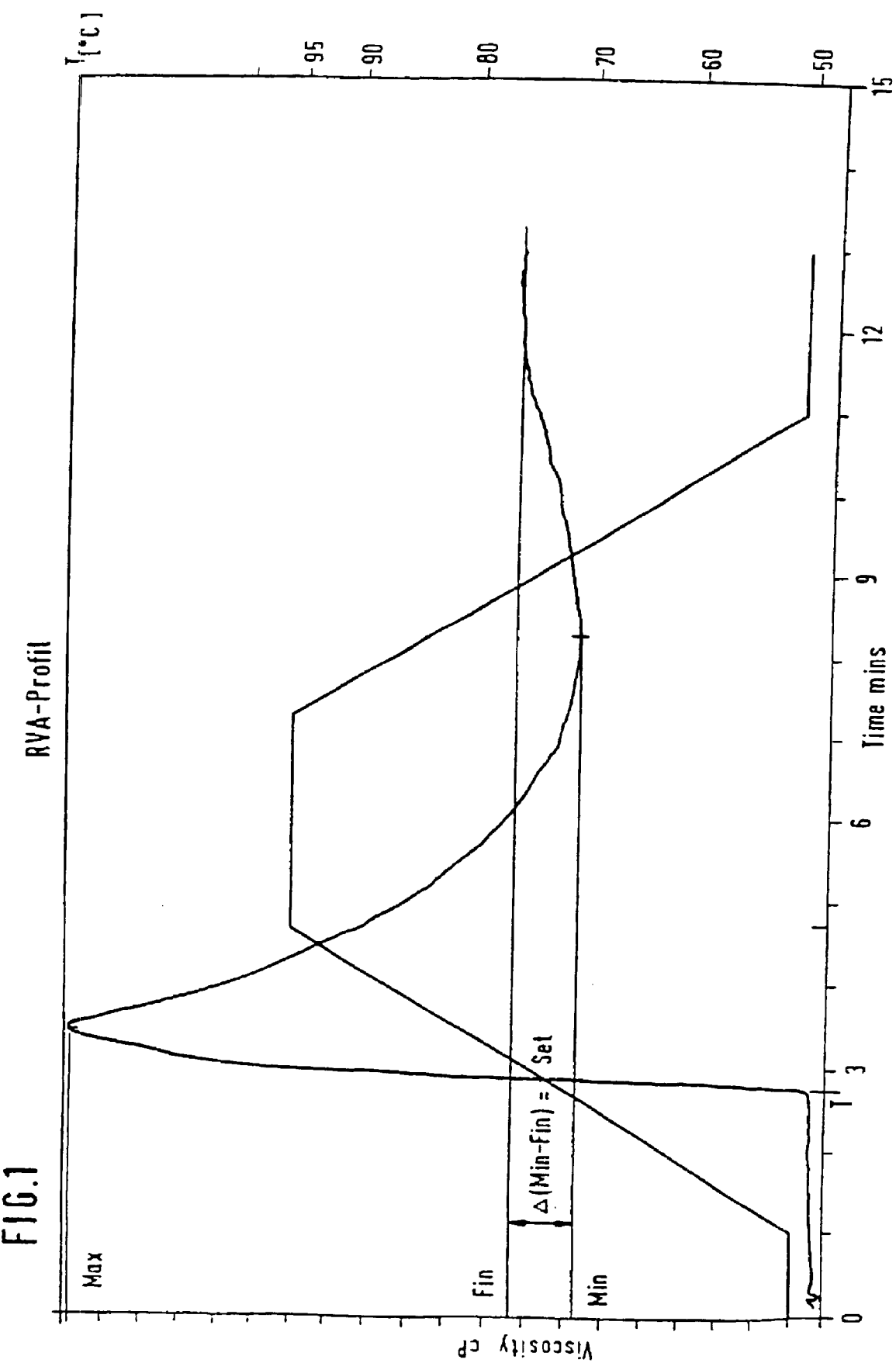
FIG. 1: is a schematic illustration of an RVA profile.

Determination of the Phosphate Content in the C6 Position of the Glucose Monomer (=C6 P Content) of the Starch (Nielsen et al. Plant Physiol. 105, (1994), 111–117)

In order to determine the C6 P content of the starch, 50 mg starch were hydrolysed in 500 µl 0.7 M HCl for 4 hours at 95° C. The batches were subsequently centrifuged for 10 min at 15500 g and the supernatants were taken off. 7 µl of the supernatants were mixed with 193 µl imidazole buffer (100 mM imidazole, pH 7.4; 5 mM $MgCl_2$, 1 mM EDTA and 0.4 mM NAD). Measurements were made in a photometer at 340 nm. After establishing the base absorption, the enzyme reaction was initiated by adding 2U glucose-6-phosphate dehydrogenase (from Leuconostoc mesenteroides, Boehringer Mannheim). The change in absorption was directly proportional to the concentration of the C-6 P content of the starch.

Determination of the Total Phosphate Content of the Starch

Before determining the total phosphate content of the starch, the starch had to be completely separated from phosphorylated non-glucans such as phospholipids. The Determination of the total phosphate content was determined by the method of Ames (Methods in Enzymology VIII, (1966), 115–118), as follows:

About 50 mg starch were treated with 30 µl of 10% ethanolic magnesium nitrate solution and were ignited for three hours in a muffle furnace. The residue was treated with 500 µl 0.5 M hydrochloric acid and incubated for 30 min at 60° C. A 20 µl aliquot was then made up to 300 µl with 0,5 M hydrochloric acid, was added to a mixture of 100 µl of 10% ascorbic acid and 600 µl of 0.42% ammonium molybdate in 1 M sulphuric acid, and was incubated for 20 min at 45° C. This was followed by a photometric determination at 820 nm using a phosphate calibration series as a standard.

Determination of the Gel Strength (Texture Analyser)

2.5 g starch (TS) were conglutinated in 25 ml $H_2O$ in an RVA instrument (see determination of the viscosity properties by means of a Rapid Visco Analyzer (RVA)) and were subsequently stored for 24 hours at room temperature. The samples were fixed under the sensor (a cylindrical plunger with a planar surface) of a TA-XT2 texture analysers supplied by Stable Micro Systems (Surrey, UK) and the gel strength was determined using the following instrument settings:

| | |
|---|---|
| Test speed | 0.5 mm/s |
| Depth of penetration | 7 mm |
| Contact area | 113 $mm^2$ |
| Pressure | 2 g |

Determination of the Viscosity Properties (e.g. Final Viscosity) by Means of a Rapid Visco Analyzer (RVA)

2.5 g starch (dry weight) were taken up in 25 ml $H_2O$ and used for analysis in a Rapid Visco Analyzer (Newport Scientific Pty Ltd., Investment Support Group, Warriewod NSW 2102, Australia). The instrument was operated according to the manufacturer's instructions. In order to determine the viscosity of the aqueous solution of the starch, the starch suspension was first heated for one minute to a temperature of 50° C. and was then heated from 50° C. to 95° C. at a rate of 12° C. per minute. The temperature was subsequently held for 2.5 minutes at 95° C. Thereafter, the solution was cooled from 95° C. to 50° C. at a rate of 12° C. per minute. Finally, the temperature was held for a further 6 minutes at 50° C. The viscosity was determined over the entire duration of the test.

Isolation of the Amylose Component of the Starch by Aqueous Leaching

It is known that amylose can be obtained from starch by aqueous leaching (Roger and Colonna (International Journal of Biological Macromolecules 19, (1996), 51–61). In orde to isolate the amylose component of the starch, 25 ml of an aqueous starch suspension (10% w/v) were prepared and heated in an RVA (Newport Scientific) with stirring, using the following profile:

| Time [min] | Type | Value [° C.] or [rpm] |
|---|---|---|
| 0 | Temp | 30° |
| 0 | Speed | 960 rpm |
| 0.5 | Speed | 300 rpm |
| 10 | Temp | 95° |

Directly after the viscosity of the suspension or solution exceeded 200 cP, the programme was terminated and the starch suspension or solution was transferred into a cold, 50 ml reaction vessel, mixed with 25 ml of cold water and cooled for 10 min in an ice bath to about room temperature (RT). Thereafter, the undissolved glucan was formed into a pellet by centrifugation (20 min at 2300 g at RT) and the clear supernatant was treated with 10 mg NaCl/ml. The dissolved glucan was then precipitated on to ice from 80% ethanol, was washed with ethanol again, and was dried for 3 days at 37° C. The pellet was subsequently ground (15 s 30 Hz with tungsten carbide balls in a in a vibrating mill supplied by Retsch, Germany), and 25 mg of the pellet was suspended in 500 µl of 0.7M HCl hydrolysed at 95° C. for 4 hours. Undissolved particles were then removed by centrifugation and the content of glucose-6P was determined enzymatically (see above: "Determination of the phosphate content in the C6 position of the glucose monomer").

Procedure for the Small Scale Water Absorption Test on Wheat Flour

Materials

Eppendorf cups (2 ml) with screw cap from Sarsted.

Eppendorf centrifuge (Sigma 202)

Vortex (Wilten)

Analytical Balance (Mettler)

Method

Measure the weight of the epp cup to four decimal places using the analytical balance.

Fill the cup with 100 to 110 mg flour and note the exact weight.

Put the cup with flour on the vortex and add 1.0 ml water during vortexing.

Keep on vortexing for 10 seconds.

Add 0.9 ml water and close the cup with the screw cap.

Wait ten minutes.

Put the cups in the 6*10 rotor (swing out) in the centrifuge.

Run the centrifuge for 30 minutes at 10,000 rpm (about 8600*g).

Pour off the water from the cup.

Dry the inside of the cup with filter paper without disturbing the wet residue.

Measure the weight of the Eppendorf cup with the wet flour to four decimal places using the analytical balance.

Calculate the weight of the absorbed water.

Determine the water absorption of each flour ten times and calculate the average.

Differential Scanning Calorimetry

Differential Scanning Calorimetry (DSC) is a technique studying thermal transitions, in this case of breadcrumbs.

With this technique the heat flow into a sample is determined at a continuous (relatively low) heating rate. Either a peak (offset from the base line (endotherm)) or a step in the base line (glass transition) determines transitions.

Integration of the peak area with respect to the base line gives the enthalpy of the transition. For breadcrumbs, an amylopectin heat of fusion between 40 and 70° C. (60° C. peak) and an amylose-lipid decomplexation at about 120° C. are generally observed.

Differences in the heat of fusion of amylopectin between the various flour samples indicate differences in retrogradation behaviour, and hence indicate that the bread is becoming stale. The enthalpy of fusion of the amylopectin crystals increases with storage time after baking. An increase in the enthalpy of fusion during storage is a measure of an increase in the amount of recrystallised amylopectin with time. The enthalpies (j/g) were calculated on a dry matter basis in order to correct for differences in moisture content.

DSC measurements were made using a TA Instruments Type 2920 calorimeter with LNCA cooling unit. This cooling unit uses liquid nitrogen for fast cooling after the experiment.

Samples (40–50 mg breadcrumbs) were placed in a DSC pan and compressed by hand with a nail. After sealing the DSC pan with a compression unit the sample was placed in the DSC-apparatus.

Samples (40–50 mg breadcrumbs) were heated from 20° C. to 160° C. at a rate of 7.5 C/min in stainless steel hermetically sealed pans (Perkin Elmer). A medium pressure pan (120 µl volume), filled with 100 mg aluminium, was used as a reference.

The enthalpies of the crumbs of the mini-loaves were measured after 1, 3, 7 and 14 days of storage in single measurements.

The following examples serve to explain the invention without limiting it in any respect:

EXAMPLE 1

Production of Vector pUbiR1 for the Transformation of Wheat Plants

Figure 2:
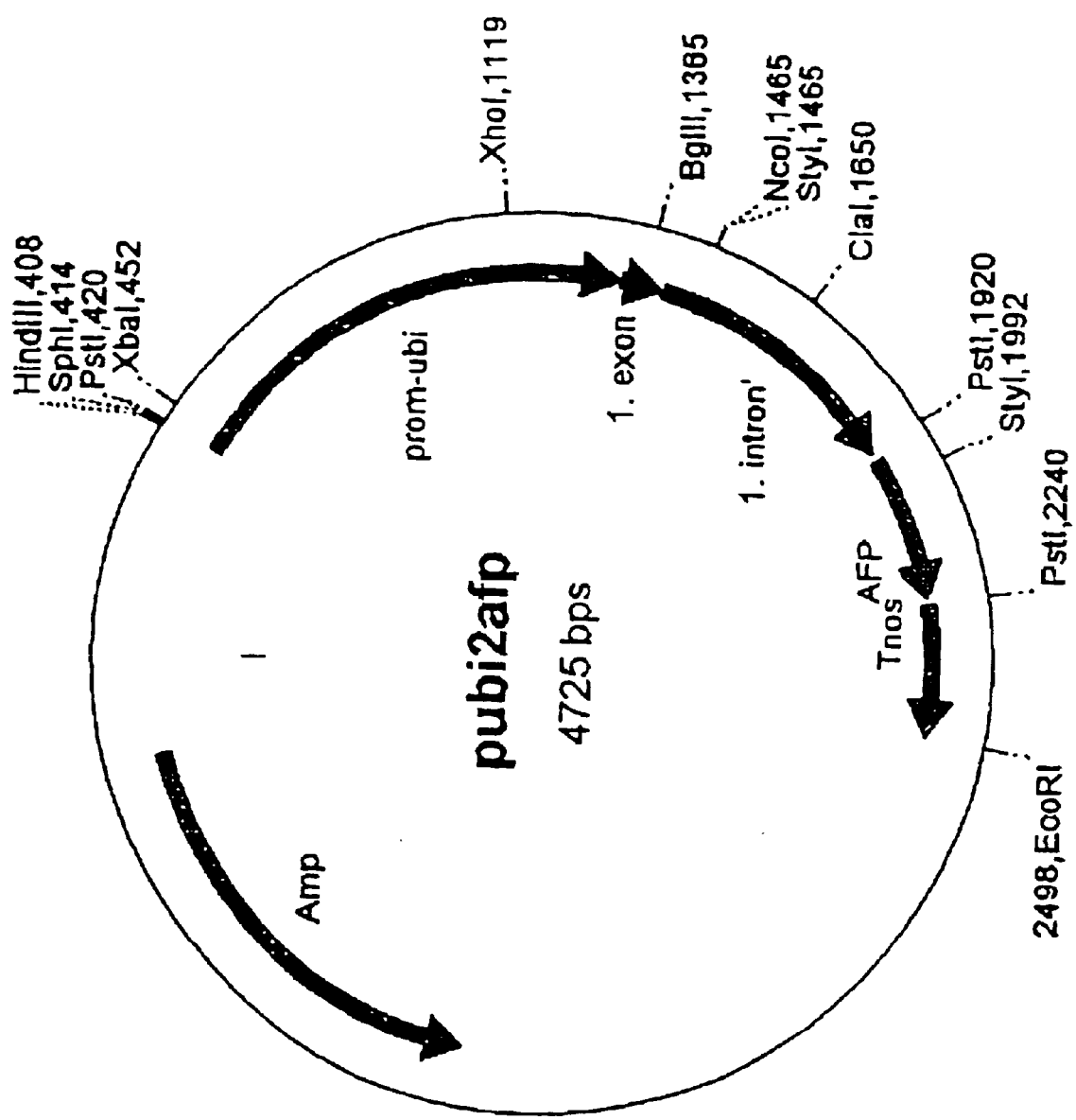
FIG. 2: is a plasmid map of the vector pUbi2afp

In order to produce vector pUbiR1, vector pUbi.cas was first produced as follows: Vector pUbi2afp (see FIG. 2) was partially cut with restriction enzymes PstI/EcoRI. The 4.19 Kb fragment which resulted therefrom, consisting of the pUC19 vector (Yannish-Perron et al., 1985, Gene 33: 103–119), the 1.5 Kb ubiquitin promoter and of the first exon of the ubi gene and a shortened ubiquitin 1 intron (ClaI deletion) (Christensen et al., Plant Mol. Biol. 18, (1992), 675–689) was used further after gel elution.

The nos terminator was isolated as a PstI/EcoRI fragment from the vector pAct.cas (Product Number Cambia TG0063, supplied by Cambia, GPO Box 3200, Canberra ACT 2601, Australia) and ligation of the two fragments was effected to give the vector pUbi.cas.

Figure 3:
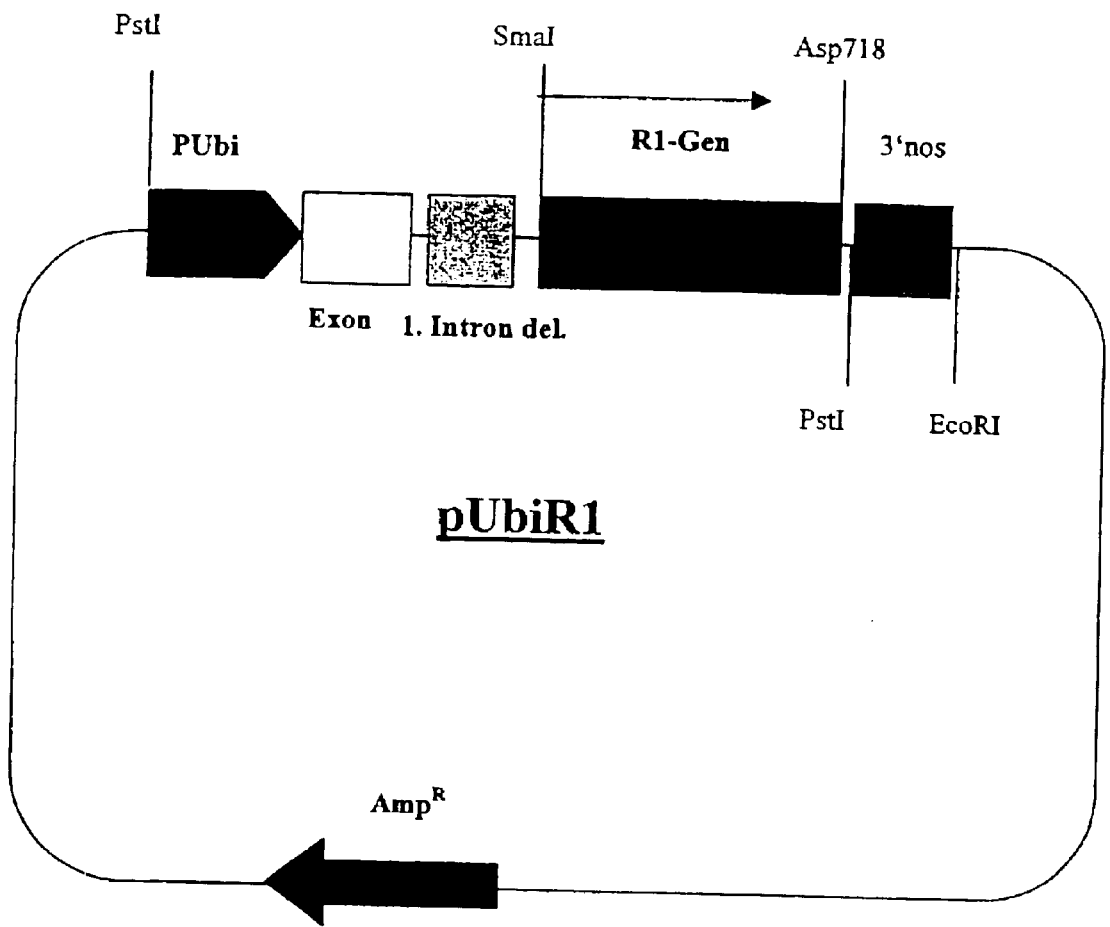
FIG. 3: is a plasmid map of the vector pUbiR1

The cDNA of the potato R1 gene (SEQ ID No.1) was subsequently isolated as a partial digest (SmaI/Asp718 fragment) from the vector pRL2 (WO97/11188, Example 4, deposited at the German Collection for Microorganisms with the number DSM 10225) and was integrated in the vector pUbi cas (restriction with SmaI/Asp718). The resulting construct was designated as pUbiR1 (see FIG. 3). This construct comprises the coding region of the R1 cDNA from potatoes, which is under the control of the ubiquitin promoter (Christensen et al., 1992, Plant Mol. Biol. 18: 675–689), and also comprises, as additional regulation units, the first exon of the ubi gene (Christensen et al., Plant Mol. Biol. 18, (1992), 675–689) and the shortened first intron (Christensen et al., Plant Mol. Biol. 18, (1992), 675–689), the internal ClaI fragment being deleted).

EXAMPLE 2

Figure 4:
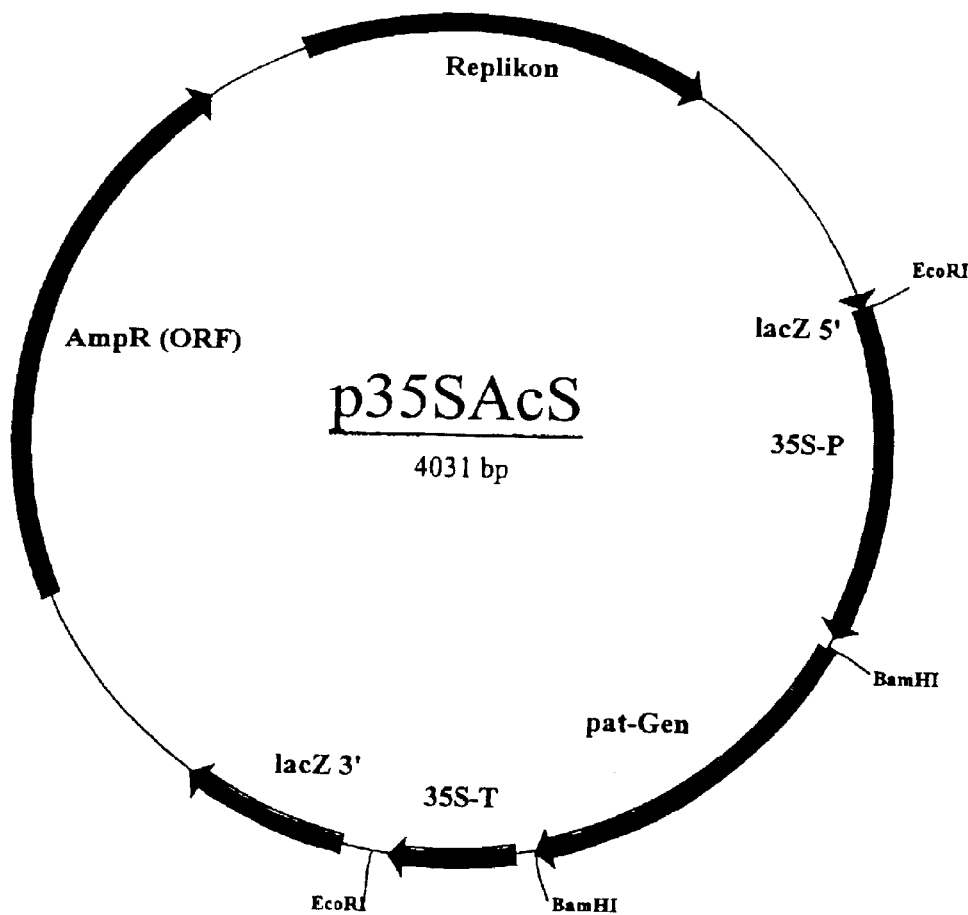
FIG. 4: is a plasmid map of the vector p35SAcS (a derivative of pUC18 (Pietrzak M. et al., Nucleic Acids Res.14, (1986), 5857–5868): contains the pat gene from Streptomyces viridochromogenes (Wohlleben et al., Gene 70, (1988), 25–37) under the control of the CaMV35S promoter.
Figure 5:
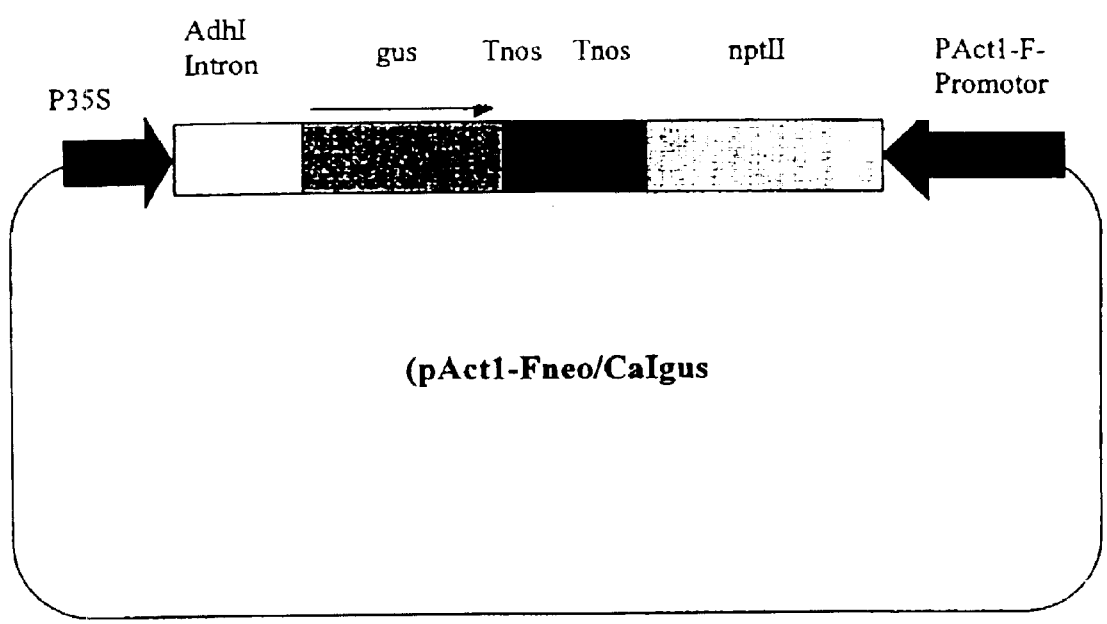
FIG. 5: is a plasmid map of the vector pAct1-Fneo/Calgus (pUC19-derivative (Yannish-Perron et al., 1985, Gene 33: 103–119): formed from pAct1-Fneo (Müller et al., Plant Science 114, (1996), 71–82) and pCalgus, which contains the CaMV35S promoter (see U.S. Pat. No. 5,352,605, for example), the Adh1 intron from maize (Genes Dev 1987 December;1(10):1183–200) and the beta-glucuronidase (GUS) gene (The GUS Reporter System as a Tool to Study Plant Gene expression in: GUS Protocols: Using the GUS Gene as a Reporter of Gene expression, Academic Press (1992), 23–43).

Production of Wheat Plants which Express an R1 Gene from Solanum Tuberosum, and Analysis of the Phosphate Content of the Starch of these Plants The biolistic transformation method was used for the transformation of wheat (Becker et al., Plant J. 5 (2), (1994), 229–307). The vector pUbiR1 and, for biolistic cotransformation, the vectors p35SAcS (see FIG. 4) or pAct1-Fneo/Calgus (Müller et al., Plant Science 114, (1996), 71–82, see FIG. 5) were used in identical molar ratios in the DNA particle precipitation batch.

Vector p35SAcS was produced as follows: The pat gene from *S. viridochromogenes* (Wohlleben et al., Gene 70, (1988), 25–37) was amplified via a polymerase chain reaction. The primers used were designed so that a BamHI cleavage site was created on both sides of the amplificate. The BamHI fragment was subsequently cloned into the BamHI cleavage site placed between the 35S promoter and the 35S terminator of the vector pDH51 (Pietzrak et al., Nucleic Acids Res. 14, (1986), 5857–5868). The cassette containing the 35S promoter, the pat gene and the 35S terminator was cut as an EcoRI fragment and was cloned into in the EcoRI cleavage site of the vector pUC18 (Pietzrak et al., Nucleic Acids Res. 14, (1986), 5857–5868). Scutelli from 14-day old, unripe embryos of wheat plants were used as target cells for transformation. Transformation was followed by in vitro culture on MS medium (PCT/EP97/02793) containing 2 mg/l 2,4-D (=2,4-dichlorophenoxyacetic acid). Two weeks after transformation, subculture was effected on the same medium, to which 2 mg/l phosphinotricin or 150 mg/l kanamycin sulphate had been added. After a further two weeks, the developing calli were transplanted on to a regeneration medium (MS⁻ medium with 0.1 mg/l 2,4-D and 2 mg/l PPT or 150 mg/l kanamycin). The developing shoots were transferred to semi-concentrated MS⁻ medium without 2,4-D and phosphinotricin or kanamycin and were subsequently transferred into the ground. About 14 days after their establishment in the ground, the transgenic plants were identified by spraying twice with an aqueous solution containing 150 and 200 mg/l phosphinotricin, respectively, 0.1% Tween 20 (ICI America, corresponding to polysorbate 20) or by spraying twice with 2.5% kanamycin sulphate, 0.1% Tween 20.

Expression of the Potato R1 Gene in $T_0$ Plants

Expression of the potato R1 gene in transgenic wheat $T_0$ plants was detected by Northern and Western blotting analyses and by the enzymatic determination of the phosphate content in the C6 position of the glucose monomer of the starch from caryopses (Nielsen et al., Plant Physiol. 105, (1994), 111–117).

R1 protein was detected in the transgenic wheat plants with the aid of an anti-potato R1 protein antibody (Ritte et al., Plant J. 21(4), (2000), 387–391).

Protein extracts from the endosperm of unripe caryopses about 20 days old was used for screening the transgenic plants.

Starch from transgenic $T_0$ plants was isolated from unripe and ripe wheat caryopses in order to determine C6 phosphate. The caryopses were triturated in a mortar to form a powder. After adding 15 ml of 100 mM Tris buffer, pH 8.0, the suspension was filtered through a 100 μm sieve and the starch was pelletised by centrifugation (2600 g, 5 min, 4° C.). The supernatant was discarded. The starch pellet was subsequently re-suspended in 2 ml of 100 mM Tris buffer, pH 8.0 and transferred to an 8 ml Percoll gradient. The starch was palletised by centrifugation for 15 minutes at 170 g and 4° C. The starch pellet was subsequently washed three times with 10 ml of 100 Tris buffer, pH 8.0. Finally, the starch was degreased by acetone incubation and was dried.

The C6 P content was determined by glucose-6-phosphate determination by means of an optical-enzymatic test (Nielsen et al., Plant Physiol. 105, (1994), 111–117) in the manner described above.

The tests showed that of the wheat $T_0$ plants which gave a positive result in Southern blotting analysis about 50% of the lines in the caryopses synthesised a starch which had an increased phosphate content in the C6 position of the glucose monomer compared with starch from corresponding non-genetically modified wild-type-plants of the Florida variety. Table 1 gives the data for some selected lines.

Analysis of Natural Descendants

Seeds which were obtained naturally from R1-expressing parental lines was sown and the segregation ratios were determined. It was possible to detect both the integration and also the expression of the R1 gene in $T_1$ descendants of different lines by Southern and Northern blotting analyses. The phosphate content of these lines in the C6 position of the starch was determined. Table 1 shows the data for some selected lines.

TABLE 1

| Line No. | C6 P in nmol/mg | Generation | Standard deviation |
| --- | --- | --- | --- |
| Wild-type Florida variety | Not detectable | — | 0.0 |
| 19 | 2.8 | T0 | 0.2 |
| 20–25 | 6.7 | T1 | 0.2 |
| 37 | 1.4 | T0 | 0.3 |
| 40A-11-8 | 10.7 | T2 | 0.7 |

EXAMPLE 3

RVA Analysis of the Starch of Plants from Transgenic Wheat Plants which Express an R1 Gene from Solanum Tuberosum, and Investigation of the Gel Strength The starches from the wheat plants described in Examples 1 and 2 were subjected to an RVA analysis.

The results of the RVA analysis (experimental: see methods) showed that the viscosity behaviour of the starches from the transgenic wheat plants which express an R1 gene from Solanum tuberosum is significantly modified compared with starches from corresponding non-genetically modified wild-type-wheat plants (Florida variety) (see Table 2).

TABLE 2

| Line No. | RVA Max (%) | RVA Min (%) | RVA Fin (%) | RVA Set (%) | RVA T (%) |
| --- | --- | --- | --- | --- | --- |
| Wild-type (Florida) | 100 | 100 | 100 | 100 | 100 |
| 19 (T0) | 98.7 | 113.8 | 116.8 | 120.7 | 102 |
| 20–25 (T1) | 155.3 | 190 | 193.8 | 198.8 | 99 |

TABLE 2-continued

| Line No. | RVA Max (%) | RVA Min (%) | RVA Fin (%) | RVA Set (%) | RVA T (%) |
| --- | --- | --- | --- | --- | --- |
| 37 (T0) | 143.8 | 156.2 | 148.8 | 139 | 101 |
| 40-11-8 (T2) | 156.2 | 185.5 | 187.7 | 190.6 | 97 |

Legend:
RVA = Rapid Visco Analyzer
Max = see FIG. 1
Min = see FIG. 1
Fin = final viscosity, see FIG. 1
Set = Setback = Difference between Min and Fin, see FIG. 1
T = Conglutination temperature, see FIG. 1
The percentages are given with respect to the wild-type (=100%).

The gel strengths of the starches (determination of the gel strength: see methods) from the transgenic wheat plants which express an R1 gene from Solanum tuberosum differed both from those of starches from corresponding non-genetically modified wild-type-wheat plants (Florida variety) and from those of wild-type-starches (Florida variety), which had subsequently been chemically phosphorylated (see Table 3).

In contrast to chemically phosphorylated starches with a comparable phosphate content in the C6 position of the glucose monomer, after conglutination the gels of the starches according to the invention exhibited an increased gel strength compared with gels of starches of wild-type-plants. In contrast to this, the chemically phosphorylated starches which had been produced by the method described by Lim compared with gels of starches of wild-type plants.

TABLE 3

| Line No. | Gel strength (TA) (%) | Phosphate content in the C6 position in μmol phosphate/g starch |
| --- | --- | --- |
| Wild-type (Florida) | 100 | Not detectable |
| 19 (T0) | 167 | 2.8 |
| 20–25 (T1) | 192 | 6.7 |
| 37 (T0) | 168 | 1.4 |
| 40-11-8 (T2) | 224 | 10.7 |
| Chemically phosphorylated wild-type (Florida) starch | | |
| STMP1 | 84 | 2.1 |
| STMP6 | 75 | 6.5 |
| STMP8 | 67 | 11.5 |

TA = texture analyzer
The percentages are given with respect to the wild-type (=100%).

EXAMPLE 4

DSC Analysis of the Starch of Plants from Transgenic Wheat Plants which Express an R1 Gene from Solanum Tuberosum The starches from the wheat plants described in Examples 1 and 2 were subjected to DSC analysis.

The peak temperature was determined using an instrument supplied by Perkin Elmer (instrument designation: DSC-7) using large volume capsules, wherein the sample to be investigated had a ratio of starch to total water content of about 1:4 and measurements were made over the temperature range from 10° C. to 160° C. at a heating rate of 10° C./min.

The results of the DSC analysis (Table 4) show that the peak temperature of the starches from the transgenic wheat plants which express an R1 gene from Solanum tuberosum exhibit a reduced peak temperature Tp compared with starches from corresponding non-genetically modified wildtype-wheat plants (Florida variety) and also compared with starches of comparable phosphate content in the C6 position of the glucose monomer which were subsequently chemically phosphorylated.

TABLE 4

| Sample | Water content of sample (%) | Starch (dry weight):water (total water content) | Peak temperature in ° C. (first peak maximum) | Other peak maxima in ° C. |
|---|---|---|---|---|
| Wild-type (Florida) | 16.6 | 1:4.01 | 61 | 101 |
| 19 (T0) | 10.5 | 1:3.99 | 58 | 100 |
| 20–25 (T1) | 16.9 | 1:4.05 | 55 | 100 |
| 40-11-8 (T2) | 16.9 | 1:3.98 | 56 | 100 |
| STMP2* | 10.9 | 1:4.00 | 60 | 101 |
| STMP6 | 10.7 | 1:4.00 | 61 | 101 |

*The chemically phosphorylated starch STMP2 had a phosphate content in the C6 position of 3.0 μmol phosphate/g starch. All the other phosphate data are given in Table 3.

EXAMPLE 5
Determination of the C6 P Content of the Amylose Component of Various Starches Apart from starch from transgenic wheat plants which express an R1 gene from Solanum tuberosum, two chemically phosphorylated starches (STMP3 and STPP4) were investigated. Chemical phoshorylation was effected by the method described by Lim and Seib (Cereal Chem. 70 (2), (1993), 137–144), wherein STMP3 was produced by reacting the starch for 2 hours at pH 6, and STPP4 was produced by reaction for 30 minutes at pH 8. The abbreviation STMP represents the selected phoshorylation reagent, namely sodium trimetaphosphate; STPP represents sodium tripolyphosphate.

The amylose component of various starches was isolated as described above (isolation of the amylose component of the starch by aqueous leaching). The phosphate content in the C6 position was determined as described above (determination of the phosphate content in the C6 position of the glucose monomer).

TABLE 5

| Sample | C6 P content in μmol phosphate/g starch | C6 P content in μmol phosphate/g amylose | C6 P content of amylose/C6 P content of starch |
|---|---|---|---|
| 40-11-8 (T2) | 10.7 | 1.9 | 0.18 |
| STPP4 | 20.5 | 20.4 | 0.99 |
| STMP3 | 6.0 | 5.1 | 0.85 |

It can be seen that the ratio of the C6 P content of the amylose to the C6 P content of the starch in the chemically phosphorylated starches is considerably higher than in the starches from the transgenic wheat plants which superexpress an R1 Gen from potatoes. The chemically phosphorylated starches have a higher content of phosphorylated amylose than do the starches from the transgenic wheat plants.

EXAMPLE 6
DSC Analysis of Breadcrumbs from Micro-loaves Produced from Flour of Different Origins Wheat flour from wheat wild-type plants (Florida variety) and from genetically modified-wheat plants which superexpress the R1 gene from potato was used to produce microloaves, using the following recipe:

| Wheat flour | 10.00 g |
|---|---|
| Yeast | 0.25 g |
| Salt | 0.20 g |
| Dextrose | 0.10 g |
| Ascorbic acid | 20 ppm |
| Water | the amount of water as determined in the water absorption test and corrected for consistency (see method "Procedure for small scale water absorption test on wheat flour") |

The dough of the genetically modified wheat plants became very sticky during the mixing process. To obtain doughs with correct handling properties a smaller amount of water was used. The dough consistency was corrected by technical sensory perception of the stiffness of the dough.

The dough was proofed in a proofing cabinet for 45 minutes (28° C.), manually worked through, proofed for 15 minutes (28° C.) for a second time, formed and put in a baking tin. Subsequently, the dough was given a final proof for 60 minutes (28° C.). The loaves were baked in an oven for 15 minutes (200° C.), with the tins embedded in a moist wooden frame. This embedding was done to shield the baking tin from high amounts of radiative heat. Finally, the loaves were baked for 5 minutes, without the wooden frame, to allow the crust to brown.

Differential scanning calorimetry (DSC) (see methods) was used to determine thermal transitions of the breadcrumbs. The enthalpies of crumbs from the loaves were measured after 1, 3, 7 and after 14 days of storage (FIG. 6).

Figure 6:
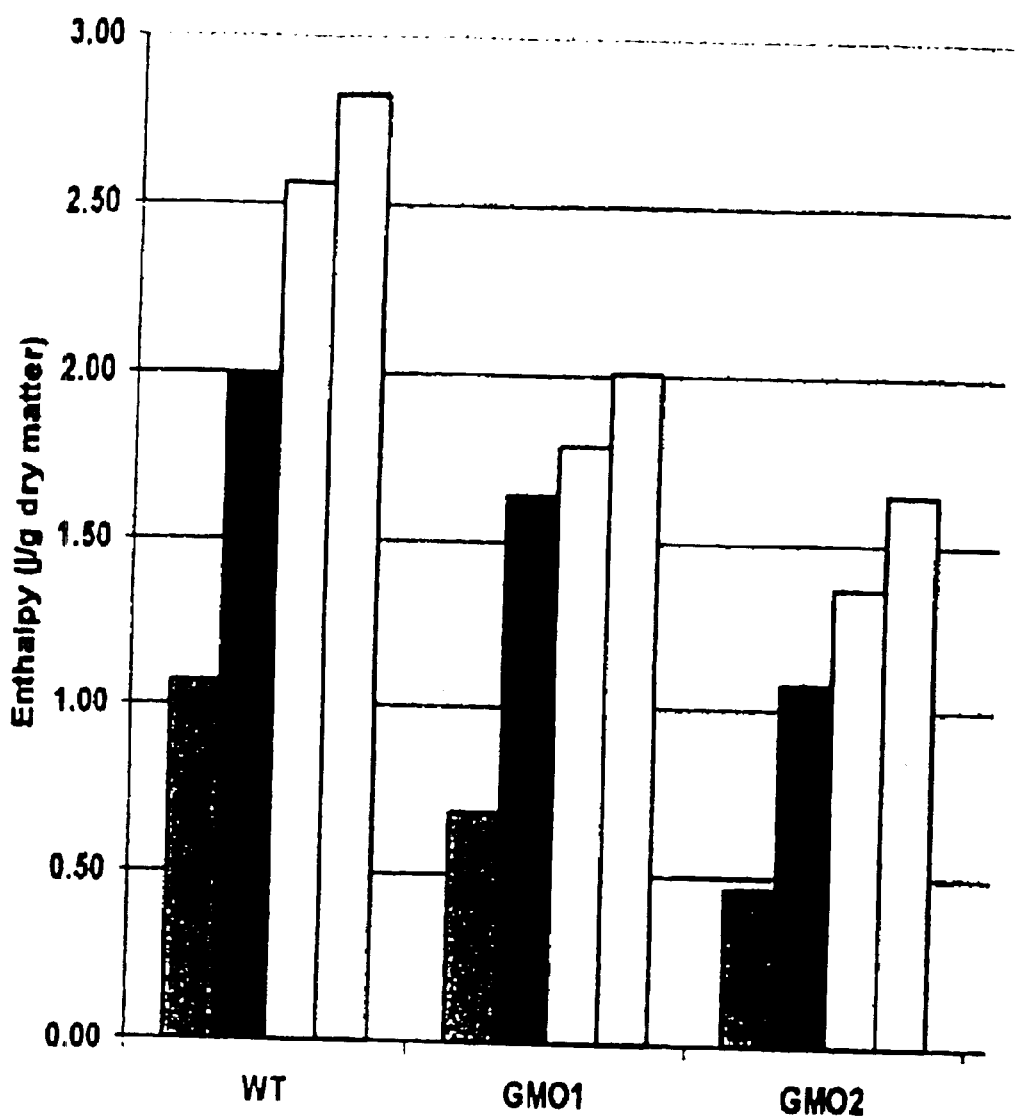
FIG. 6: shows the enthalpy of breadcrumbs during storage after 1, 3, 7 and 13 days.

FIG. 6 shows the enthalpy of the amylopectin fusion peak (40° C.–70° C.) for stored bread crumbs after 1, 3, 7 and 13 days of storage, giving an indication of staling effects. The breadcrumbs from loaves made from wild-type (Florida) flour have a higher enthalpy compared with breadcrumbs of the same age made from flour from two different lines (GMO1 and GMO2) of genetically modified wheat plants which superexpress the R1 gene from potato. This indicates a lower level of recrystallised starch, less retrogradation of starch and less staling of the bread.

What is claimed is:

1. A genetically modified monocotyledon plant cell, wherein the genetic modification consists of the introduction of at least one extraneous nucleic acid molecule and the extraneous nucleic acid molecule is selected from the group consisting of:
  (a) nucleic acid molecules which comprise the coding region of the nucleotide sequence represented in Seq ID No. 1; and
  (b) nucleic acid molecules which encode an R1 protein from Solarium tuberosum with the amino acid sequence given in Seq ID No. 2.

2. The plant cell according to claim 1, which exhibits an increased biological activity of R1 protein compared with a corresponding non-genetically modified wild-type plant cell.

3. The plant cell according to claim 1, which synthesises a starch which has an increased phosphate content in the C6 position of the glucose monomer compared with starch from corresponding non-genetically modified wild-type plant cells.

4. The plant cell according to claim 1, which synthesises a starch which has an increased final viscosity and/or a reduced peak temperature compared with starch from corresponding non-genetically modified wild-type plant cells.

5. The plant cell according to claim 1, which synthesises a starch which after conglutination forms a gel which has an increased gel strength compared with a gel of starch from corresponding non-genetically modified wild-type plant cells.

6. The plant cell according to claim 1, which originates from a plant selected from the group consisting of wheat, rice, barley, oats, millet, rye and maize.

7. The plant cell according to claim 6, which originates from a wheat plant.

8. The plant cell according to claim 7, which synthesises a starch which in the C6 position of the glucose monomer has a phosphate content of at least 0.1 nmol C6 P $mg^{-1}$ starch.

9. A method of producing a plant cell according to claim 1, wherein a cell of a monocotyledon plant is genetically modified, and wherein the genetic modification consists of the introduction of at least one extraneous nucleic acid molecule into the plant cell.

10. A plant containing plant cells according to claim 1.

11. The plant according to claim 10, which in its starch-storing organs synthesises a starch which has an increased phosphate content in the C6 position of the glucose monomer compared with starch from the starch-storing organs of corresponding non-genetically modified wild-type-plants.

12. The plant according to claim 10, which is a rice, wheat or maize plant.

13. A method of producing the plant according to claim 10, wherein
  (a) a cell of a monocotyledon plant is genetically modified, wherein the genetic modification consists of the introduction of at least one extraneous nucleic acid molecule into the cell;
  (b) a plant is regenerated from the cell according to step (a); and optionally
  (c) further plants are produced from the plant produced according to step (b).

14. The method according to claim 13, wherein the extraneous nucleic acid molecule is under the control of a promoter which organ-specifically facilitates R1 gene expression in starch-storing tissues.

15. The method according to claim 13, wherein the plant is a wheat plant.

16. A propagation material for a plant according to claim 10, which propagation material contains plant cells according to claim 1.

17. A method of producing a starch comprising the extraction of the starch from a plant cell according to claim 1 or a plant according to claim 10.

* * * * *

SEQUENCE LISTING

```
<160> NUMBER OF SEQ ID NOS: 16

<210> SEQ ID NO 1
<211> LENGTH: 5061
<212> TYPE: DNA
<213> ORGANISM: Solanum tuberosum
<220> FEATURE:
<221> NAME/KEY: CDS
<222> LOCATION: (216)..(4607)
```

<400> SEQUENCE: 1

```
gaattgtaat acgactcact atagggcgaa ttgggtaccg ggcccccct cgaggtcgac      60 ggtatcgata agcttgatat cgaattcgcg gccgcttttg cttcgtgaat tcatcttcat     120
cgaatttctc gacgcttctt cgctaatttc ctcgttactt cactagaaat cgacgtttct    180
agctgaactt gagtgaatta agccagtggg aggat atg agt aat tcc tta ggg        233
                                      Met Ser Asn Ser Leu Gly
                                       1               5 aat aac ttg ctg tac cag gga ttc cta acc tca aca gtg ttg gaa cat       281
Asn Asn Leu Leu Tyr Gln Gly Phe Leu Thr Ser Thr Val Leu Glu His
         10                  15                  20 aaa agt aga atc agt cct cct tgt gtt gga ggc aat tct ttg ttt caa       329
Lys Ser Arg Ile Ser Pro Pro Cys Val Gly Gly Asn Ser Leu Phe Gln
             25                  30                  35 caa caa gtg atc tcg aaa tca cct tta tca act gag ttt cga ggt aac       377
Gln Gln Val Ile Ser Lys Ser Pro Leu Ser Thr Glu Phe Arg Gly Asn
     40                  45                  50 agg tta aag gtg cag aaa aag aaa ata cct atg gga aag aac cgt gct       425
Arg Leu Lys Val Gln Lys Lys Lys Ile Pro Met Gly Lys Asn Arg Ala
 55                  60                  65                  70 ttt tct agt tct cct cat gct gta ctt acc act gat acc tct tct gag       473
Phe Ser Ser Ser Pro His Ala Val Leu Thr Thr Asp Thr Ser Ser Glu
                 75                  80                  85 cta gca gaa aag ttc agt cta gaa ggg aat att gag cta cag gtt gat       521
Leu Ala Glu Lys Phe Ser Leu Glu Gly Asn Ile Glu Leu Gln Val Asp
             90                  95                 100 gtt agg cct ccc act tca ggt gat gtg tcc ttt gtg gat ttt caa gct       569
Val Arg Pro Pro Thr Ser Gly Asp Val Ser Phe Val Asp Phe Gln Ala
        105                 110                 115 aca aat ggt agt gat aaa ctg ttt ttg cac tgg ggg gca gta aag ttc       617
Thr Asn Gly Ser Asp Lys Leu Phe Leu His Trp Gly Ala Val Lys Phe
    120                 125                 130 gga aaa gaa aca tgg tct ctt cct aat gat cgt cca gat ggg acc aaa       665
Gly Lys Glu Thr Trp Ser Leu Pro Asn Asp Arg Pro Asp Gly Thr Lys
135                 140                 145                 150 gtg tac aag aac aaa gca ctt aga act cca ttt gtt aaa tct ggc tct       713
Val Tyr Lys Asn Lys Ala Leu Arg Thr Pro Phe Val Lys Ser Gly Ser
                155                 160                 165 aac tcc atc ctg aga ctg gag ata cgg gac act gct atc gaa gct att       761
Asn Ser Ile Leu Arg Leu Glu Ile Arg Asp Thr Ala Ile Glu Ala Ile
            170                 175                 180 gag ttt ctc ata tac gat gaa gcc tac gat aaa tgg ata aag aat aat       809
Glu Phe Leu Ile Tyr Asp Glu Ala Tyr Asp Lys Trp Ile Lys Asn Asn
        185                 190                 195 ggt ggc aat ttt cgt gtc aaa ttg tca aga aaa gag ata cga ggc cca       857
Gly Gly Asn Phe Arg Val Lys Leu Ser Arg Lys Glu Ile Arg Gly Pro
    200                 205                 210 gat gtt tca gtt cct gag gag ctt gta cag atc caa tca tat ttg agg       905
Asp Val Ser Val Pro Glu Glu Leu Val Gln Ile Gln Ser Tyr Leu Arg
215                 220                 225                 230 tgg gag agg aag gga aaa cag aat tac acc cct gag aaa gag aag gag       953
Trp Glu Arg Lys Gly Lys Gln Asn Tyr Thr Pro Glu Lys Glu Lys Glu
                235                 240                 245 gaa tat gag gct gct cga act gag cta cag gag gaa ata gct cgt ggt      1001
Glu Tyr Glu Ala Ala Arg Thr Glu Leu Gln Glu Glu Ile Ala Arg Gly
            250                 255                 260 gct tcc ata cag gac att cga gca agg cta aca aaa act aat gat aaa      1049
Ala Ser Ile Gln Asp Ile Arg Ala Arg Leu Thr Lys Thr Asn Asp Lys
```

```
                265                 270                 275
agt caa agc aaa gaa gag cct ctt cat gta aca aag agt gaa ata cct     1097
Ser Gln Ser Lys Glu Glu Pro Leu His Val Thr Lys Ser Glu Ile Pro
        280                 285                 290 gat gac ctt gcc caa gca caa gct tac att agg tgg gag aaa gca gga     1145
Asp Asp Leu Ala Gln Ala Gln Ala Tyr Ile Arg Trp Glu Lys Ala Gly
295                 300                 305                 310 aag ccg aac tat cct cca gaa aag caa att gaa gaa ctc gaa gaa gca     1193
Lys Pro Asn Tyr Pro Pro Glu Lys Gln Ile Glu Glu Leu Glu Glu Ala
                315                 320                 325 aga aga gaa ttg caa ctt gag ctt gag aaa ggc att acc ctt gat gag     1241
Arg Arg Glu Leu Gln Leu Glu Leu Glu Lys Gly Ile Thr Leu Asp Glu
        330                 335                 340 ttg cgg aaa aag att aca aaa ggg gag ata aaa act aag gcg gaa aag     1289
Leu Arg Lys Lys Ile Thr Lys Gly Glu Ile Lys Thr Lys Ala Glu Lys
345                 350                 355 cac gtg aaa aga agc tct ttt gcc gtt gaa aga atc caa aga aag aag     1337
His Val Lys Arg Ser Ser Phe Ala Val Glu Arg Ile Gln Arg Lys Lys
        360                 365                 370 aga gac ttt ggg cag ctt att aat aag tat cct tcc agt cct gca gta     1385
Arg Asp Phe Gly Gln Leu Ile Asn Lys Tyr Pro Ser Ser Pro Ala Val
375                 380                 385                 390 caa gta caa aag gtc ttg gaa gaa cca cca gcc tta tct aaa att aag     1433
Gln Val Gln Lys Val Leu Glu Glu Pro Pro Ala Leu Ser Lys Ile Lys
                395                 400                 405 ctg tat gcc aag gag aag gag gag cag att gat gat ccg atc ctt aat     1481
Leu Tyr Ala Lys Glu Lys Glu Glu Gln Ile Asp Asp Pro Ile Leu Asn
        410                 415                 420 aaa aag atc ttt aag gtc gat gat ggg gag cta ctg gta ctg gta gca     1529
Lys Lys Ile Phe Lys Val Asp Asp Gly Glu Leu Leu Val Leu Val Ala
425                 430                 435 aag tcc tct ggg aag aca aaa gta cat ata gct aca gat ctg aat cag     1577
Lys Ser Ser Gly Lys Thr Lys Val His Ile Ala Thr Asp Leu Asn Gln
        440                 445                 450 cca att act ctt cac tgg gca tta tcc aaa agt cgt gga gag tgg atg     1625
Pro Ile Thr Leu His Trp Ala Leu Ser Lys Ser Arg Gly Glu Trp Met
455                 460                 465                 470 gta cca cct tca agc ata ttg cct cct gga tca att att tta gac aag     1673
Val Pro Pro Ser Ser Ile Leu Pro Pro Gly Ser Ile Ile Leu Asp Lys
                475                 480                 485 gct gcc gaa aca cct ttt tcc gcc agt tct tct gat ggt cta act tct     1721
Ala Ala Glu Thr Pro Phe Ser Ala Ser Ser Ser Asp Gly Leu Thr Ser
        490                 495                 500 aag gta caa tct ttg gat ata gta att gaa gat ggc aat ttt gtg ggg     1769
Lys Val Gln Ser Leu Asp Ile Val Ile Glu Asp Gly Asn Phe Val Gly
505                 510                 515 atg cca ttt gtt ctt ttg tct ggt gaa aaa tgg att aag aac caa ggg     1817
Met Pro Phe Val Leu Leu Ser Gly Glu Lys Trp Ile Lys Asn Gln Gly
        520                 525                 530 tcg gat ttc tat gtt gac ttc agt gct gca tcc aaa tta gca ctc aag     1865
Ser Asp Phe Tyr Val Asp Phe Ser Ala Ala Ser Lys Leu Ala Leu Lys
535                 540                 545                 550 gct gct ggg gat ggc agt gga act gca aag tct tta ctg gat aaa ata     1913
Ala Ala Gly Asp Gly Ser Gly Thr Ala Lys Ser Leu Leu Asp Lys Ile
                555                 560                 565 gca gat atg gaa agt gag gct cag aag tca ttt atg cac cgg ttt aat     1961
Ala Asp Met Glu Ser Glu Ala Gln Lys Ser Phe Met His Arg Phe Asn
        570                 575                 580 att gct gct gac ttg ata gaa gat gcc act agt gct ggt gaa ctt ggt     2009
Ile Ala Ala Asp Leu Ile Glu Asp Ala Thr Ser Ala Gly Glu Leu Gly
```

```
                Ile Ala Ala Asp Leu Ile Glu Asp Ala Thr Ser Ala Gly Glu Leu Gly
                            585                 590                 595 ttt act gga att ctt gta tgg atg agg ttc atg gct aca agg caa ctg       2057
Phe Thr Gly Ile Leu Val Trp Met Arg Phe Met Ala Thr Arg Gln Leu
            600                 605                 610 ata tgg aac aaa aac tat aac gta aaa cca cgt gaa ata agc aag gct       2105
Ile Trp Asn Lys Asn Tyr Asn Val Lys Pro Arg Glu Ile Ser Lys Ala
615                 620                 625                 630 cag gac aga ctt aca gac ttg ttg cag aat gct ttc acc agt cac cct       2153
Gln Asp Arg Leu Thr Asp Leu Leu Gln Asn Ala Phe Thr Ser His Pro
                635                 640                 645 caa tac cgt gaa att ttg cgg atg att atg tca act gtt gga cgt gga       2201
Gln Tyr Arg Glu Ile Leu Arg Met Ile Met Ser Thr Val Gly Arg Gly
            650                 655                 660 ggt gaa ggg gat gta gga cag cga att agg gat gaa att ttg gtc atc       2249
Gly Glu Gly Asp Val Gly Gln Arg Ile Arg Asp Glu Ile Leu Val Ile
            665                 670                 675 cag agg aaa aat gac tgc aag ggt ggt atg atg gaa gaa tgg cat cag       2297
Gln Arg Lys Asn Asp Cys Lys Gly Gly Met Met Glu Glu Trp His Gln
            680                 685                 690 aaa ttg cat aat aat act agt cct gat gat gtt gtg atc tgt cag gca       2345
Lys Leu His Asn Asn Thr Ser Pro Asp Asp Val Val Ile Cys Gln Ala
695                 700                 705                 710 ttg att gac tac atc aag agt gat ttt gat ctt ggt gtt tat tgg aaa       2393
Leu Ile Asp Tyr Ile Lys Ser Asp Phe Asp Leu Gly Val Tyr Trp Lys
                715                 720                 725 acc ctg aat gag aac gga ata aca aaa gag cgt ctt ttg agt tat gac       2441
Thr Leu Asn Glu Asn Gly Ile Thr Lys Glu Arg Leu Leu Ser Tyr Asp
            730                 735                 740 cgt gct atc cat tct gaa ccg aat ttt aga gga gat caa aag aat ggt       2489
Arg Ala Ile His Ser Glu Pro Asn Phe Arg Gly Asp Gln Lys Asn Gly
            745                 750                 755 ctt ttg cgt gat tta ggt cac tat atg aga aca ttg aag gct gtt cat       2537
Leu Leu Arg Asp Leu Gly His Tyr Met Arg Thr Leu Lys Ala Val His
        760                 765                 770 tca ggt gca gat ctt gag tct gct att gca aac tgc atg ggc tac aaa       2585
Ser Gly Ala Asp Leu Glu Ser Ala Ile Ala Asn Cys Met Gly Tyr Lys
775                 780                 785                 790 act gag gga gaa ggc ttt atg gtt gga gtc cag ata aat cct gta tca       2633
Thr Glu Gly Glu Gly Phe Met Val Gly Val Gln Ile Asn Pro Val Ser
                795                 800                 805 ggc ttg cca tct ggc ttt cag ggc ctc ctc cat ttt gtc tta gac cat       2681
Gly Leu Pro Ser Gly Phe Gln Gly Leu Leu His Phe Val Leu Asp His
            810                 815                 820 gtg gaa gat aaa aat gtg gaa act ctt ctt gag gga ttg cta gag gct       2729
Val Glu Asp Lys Asn Val Glu Thr Leu Leu Glu Gly Leu Leu Glu Ala
            825                 830                 835 cgt gag gag ctt agg ccc ttg ctt ctc aaa cca aac aac cgt cta aag       2777
Arg Glu Glu Leu Arg Pro Leu Leu Leu Lys Pro Asn Asn Arg Leu Lys
840                 845                 850 gat ctg ctg ttt ttg gac ata gca ctt gat tct aca gtt aga aca gca       2825
Asp Leu Leu Phe Leu Asp Ile Ala Leu Asp Ser Thr Val Arg Thr Ala
855                 860                 865                 870 gta gaa agg gga tat gaa gaa ttg aac aac gct aat cct gag aaa atc       2873
Val Glu Arg Gly Tyr Glu Glu Leu Asn Asn Ala Asn Pro Glu Lys Ile
                875                 880                 885 atg tac ttc atc tcc ctc gtt ctt gaa aat ctc gca ctc tct gtg gac       2921
Met Tyr Phe Ile Ser Leu Val Leu Glu Asn Leu Ala Leu Ser Val Asp
                890                 895                 900
```

-continued

| | |
|---|---|
| gat aat gaa gat ctt gtt tat tgc ttg aag gga tgg aat caa gct ctt<br>Asp Asn Glu Asp Leu Val Tyr Cys Leu Lys Gly Trp Asn Gln Ala Leu<br>     905                     910                   915 | 2969 |
| tca atg tcc aat ggt gga gac aac cat tgg gct tta ttt gca aaa gct<br>Ser Met Ser Asn Gly Gly Asp Asn His Trp Ala Leu Phe Ala Lys Ala<br>920                       925                   930 | 3017 |
| gta ctt gac aga atc cgt ctt gca ctt gca agc aag gca gag tgg tac<br>Val Leu Asp Arg Ile Arg Leu Ala Leu Ala Ser Lys Ala Glu Trp Tyr<br>935                   940                 945                 950 | 3065 |
| cat cac tta ttg cag cca tct gcc gaa tat cta gga tca atc ctt ggg<br>His His Leu Leu Gln Pro Ser Ala Glu Tyr Leu Gly Ser Ile Leu Gly<br>              955                     960                  965 | 3113 |
| gtg gac caa tgg gct ttg aac ata ttt act gaa gaa att ata cgt gct<br>Val Asp Gln Trp Ala Leu Asn Ile Phe Thr Glu Glu Ile Ile Arg Ala<br>970                       975                   980 | 3161 |
| gga tca gca gct tca tta tcc tct ctt ctt aat aga ctc gat ccc gtg<br>Gly Ser Ala Ala Ser Leu Ser Ser Leu Leu Asn Arg Leu Asp Pro Val<br>985                       990                   995 | 3209 |
| ctt cgg aaa act gca aat cta gga agt tgg cag att atc agt cca gtt<br>Leu Arg Lys Thr Ala Asn Leu Gly Ser Trp Gln Ile Ile Ser Pro Val<br>     1000                   1005                 1010 | 3257 |
| gaa gcc gtt gga tat gtt gtc gtt gtg gat gag ttg ctt tca gtt cag<br>Glu Ala Val Gly Tyr Val Val Val Val Asp Glu Leu Leu Ser Val Gln<br>1015                 1020                 1025                 1030 | 3305 |
| aat gaa atc tac aag aag ccc acg atc tta gta gca aac tct gtt aaa<br>Asn Glu Ile Tyr Lys Lys Pro Thr Ile Leu Val Ala Asn Ser Val Lys<br>               1035                 1040                 1045 | 3353 |
| gga gag gag gaa att cct gat ggt gct gtt gcc ctg ata aca cca gac<br>Gly Glu Glu Glu Ile Pro Asp Gly Ala Val Ala Leu Ile Thr Pro Asp<br>1050                 1055                 1060 | 3401 |
| atg cca gat gtt ctt tca cat gtt tct gtt cga gct aga aat ggg aag<br>Met Pro Asp Val Leu Ser His Val Ser Val Arg Ala Arg Asn Gly Lys<br>               1065                 1070                 1075 | 3449 |
| gtt tgc ttt gct aca tgc ttt gat ccc aat ata ttg gct gac ctc caa<br>Val Cys Phe Ala Thr Cys Phe Asp Pro Asn Ile Leu Ala Asp Leu Gln<br>1080                 1085                 1090 | 3497 |
| gca aag gaa gga agg att ttg ctc tta aag cct aca cct tca gac ata<br>Ala Lys Glu Gly Arg Ile Leu Leu Leu Lys Pro Thr Pro Ser Asp Ile<br>1095                 1100                 1105                 1110 | 3545 |
| atc tat agt gag gtg aat gag att gag ctc caa agt tca agt aac ttg<br>Ile Tyr Ser Glu Val Asn Glu Ile Glu Leu Gln Ser Ser Ser Asn Leu<br>               1115                 1120                 1125 | 3593 |
| gta gaa gct gaa act tca gca aca ctt aga ttg gtg aaa aag caa ttt<br>Val Glu Ala Glu Thr Ser Ala Thr Leu Arg Leu Val Lys Lys Gln Phe<br>1130                 1135                 1140 | 3641 |
| ggt ggt tgt tac gca ata tca gca gat gaa ttc aca agt gaa atg gtt<br>Gly Gly Cys Tyr Ala Ile Ser Ala Asp Glu Phe Thr Ser Glu Met Val<br>               1145                 1150                 1155 | 3689 |
| gga gct aaa tca cgt aat att gca tat ctg aaa gga aaa gtg cct tcc<br>Gly Ala Lys Ser Arg Asn Ile Ala Tyr Leu Lys Gly Lys Val Pro Ser<br>1160                 1165                 1170 | 3737 |
| tcg gtg gga att cct acg tca gta gct ctt cca ttt gga gtc ttt gag<br>Ser Val Gly Ile Pro Thr Ser Val Ala Leu Pro Phe Gly Val Phe Glu<br>1175                 1180                 1185                 1190 | 3785 |
| aaa gta ctt tca gac gac ata aat cag gga gtg gca aaa gag ttg caa<br>Lys Val Leu Ser Asp Asp Ile Asn Gln Gly Val Ala Lys Glu Leu Gln<br>               1195                 1200                 1205 | 3833 |
| att ctg acg aaa aaa cta tct gaa gga gac ttc agc gct ctt ggt gaa<br>Ile Leu Thr Lys Lys Leu Ser Glu Gly Asp Phe Ser Ala Leu Gly Glu<br>1210                 1215                 1220 | 3881 |

-continued

| | |
|---|---|
| att cgc aca acg att tta gat ctt tca gca cca gct caa ttg gtc aaa<br>Ile Arg Thr Thr Ile Leu Asp Leu Ser Ala Pro Ala Gln Leu Val Lys<br>    1225              1230              1235 | 3929 |
| gag ctg aag gaa aag atg cag ggt tct ggc atg cct tgg cct ggt gat<br>Glu Leu Lys Glu Lys Met Gln Gly Ser Gly Met Pro Trp Pro Gly Asp<br>1240              1245              1250 | 3977 |
| gaa ggt cca aag cgg tgg gaa caa gca tgg atg gcc ata aaa aag gtg<br>Glu Gly Pro Lys Arg Trp Glu Gln Ala Trp Met Ala Ile Lys Lys Val<br>1255              1260              1265              1270 | 4025 |
| tgg gct tca aaa tgg aat gag aga gca tac ttc agc aca agg aag gtg<br>Trp Ala Ser Lys Trp Asn Glu Arg Ala Tyr Phe Ser Thr Arg Lys Val<br>        1275              1280              1285 | 4073 |
| aaa ctg gat cat gac tat ctg tgc atg gct gtc ctt gtt caa gaa ata<br>Lys Leu Asp His Asp Tyr Leu Cys Met Ala Val Leu Val Gln Glu Ile<br>    1290              1295              1300 | 4121 |
| ata aat gct gat tat gca ttt gtc att cac aca acc aac cca tct tcc<br>Ile Asn Ala Asp Tyr Ala Phe Val Ile His Thr Thr Asn Pro Ser Ser<br>        1305              1310              1315 | 4169 |
| gga gac gac tca gaa ata tat gcc gag gtg gtc agg ggc ctt ggg gaa<br>Gly Asp Asp Ser Glu Ile Tyr Ala Glu Val Val Arg Gly Leu Gly Glu<br>    1320              1325              1330 | 4217 |
| aca ctt gtt gga gct tac cca gga cgt gct ttg agt ttt atc tgc aag<br>Thr Leu Val Gly Ala Tyr Pro Gly Arg Ala Leu Ser Phe Ile Cys Lys<br>1335              1340              1345              1350 | 4265 |
| aaa aag gat ctc aac tct cct caa gtg tta ggt tac cca agc aaa ccg<br>Lys Lys Asp Leu Asn Ser Pro Gln Val Leu Gly Tyr Pro Ser Lys Pro<br>        1355              1360              1365 | 4313 |
| atc ggc ctt ttc ata aaa aga tct atc atc ttc cga tct gat tcc aat<br>Ile Gly Leu Phe Ile Lys Arg Ser Ile Ile Phe Arg Ser Asp Ser Asn<br>    1370              1375              1380 | 4361 |
| ggg gaa gat ttg gaa ggt tat gcc ggt gct ggc ctc tac gac agt gta<br>Gly Glu Asp Leu Glu Gly Tyr Ala Gly Ala Gly Leu Tyr Asp Ser Val<br>1385              1390              1395 | 4409 |
| cca atg gat gag gag gaa aaa gtt gta att gat tac tct tcc gac cca<br>Pro Met Asp Glu Glu Glu Lys Val Val Ile Asp Tyr Ser Ser Asp Pro<br>    1400              1405              1410 | 4457 |
| ttg ata act gat ggt aac ttc cgc cag aca atc ctg tcc aac att gct<br>Leu Ile Thr Asp Gly Asn Phe Arg Gln Thr Ile Leu Ser Asn Ile Ala<br>1415              1420              1425              1430 | 4505 |
| cgt gct gga cat gct atc gag gag cta tat ggc tct cct caa gac atc<br>Arg Ala Gly His Ala Ile Glu Glu Leu Tyr Gly Ser Pro Gln Asp Ile<br>        1435              1440              1445 | 4553 |
| gag ggt gta gtg agg gat gga aag att tat gtc gtt cag aca aga cct<br>Glu Gly Val Val Arg Asp Gly Lys Ile Tyr Val Val Gln Thr Arg Pro<br>    1450              1455              1460 | 4601 |
| cag atg tgatcatatt ctcgttgtat gttgttcaga aagaccata gatgtgatca<br>Gln Met | 4657 |
| tattctcatg gtatcagatc tgtgaccact tacctcccat gaagttgcct gtatgattat | 4717 |
| acgtgatcca aagccatcac atcatgttca ccttcagcta ttggaggaga agtgagaagt | 4777 |
| aggaattgca atatgaggaa taataagaaa aactttgtag aagttaaatt agctgggtat | 4837 |
| gatataggga gaaatgtgta aacattgtac tatatatagt atacacacgc attatgtatt | 4897 |
| tgcattatgc actgaataat atcgcagcat caaagaagaa atcctttgag tggtttcaat | 4957 |
| tgccgcggcc gcgaattcct gcagcccggg ggatccacta gttctagagc ggccgccacc | 5017 |
| gcggtggagc tccagctttt gttccctta gtgagggtta attt | 5061 |

<210> SEQ ID NO 2
<211> LENGTH: 1464
<212> TYPE: PRT
<213> ORGANISM: Solanum tuberosum

<400> SEQUENCE: 2

| | | | | | | | | | | | | | | |
|---|---|---|---|---|---|---|---|---|---|---|---|---|---|---|
| Met | Ser | Asn | Ser | Leu | Gly | Asn | Asn | Leu | Leu | Tyr | Gln | Gly | Phe | Leu | Thr |
| 1 | | | | 5 | | | | | 10 | | | | | 15 | |
| Ser | Thr | Val | Leu | Glu | His | Lys | Ser | Arg | Ile | Ser | Pro | Pro | Cys | Val | Gly |
| | | | 20 | | | | | 25 | | | | | 30 | | |
| Gly | Asn | Ser | Leu | Phe | Gln | Gln | Val | Ile | Ser | Lys | Ser | Pro | Leu | Ser | |
| | | 35 | | | | | 40 | | | | | 45 | | | |
| Thr | Glu | Phe | Arg | Gly | Asn | Arg | Leu | Lys | Val | Gln | Lys | Lys | Lys | Ile | Pro |
| | 50 | | | | | 55 | | | | | 60 | | | | |
| Met | Gly | Lys | Asn | Arg | Ala | Phe | Ser | Ser | Pro | His | Ala | Val | Leu | Thr | |
| 65 | | | | | 70 | | | | | 75 | | | | | 80 |
| Thr | Asp | Thr | Ser | Ser | Glu | Leu | Ala | Glu | Lys | Phe | Ser | Leu | Glu | Gly | Asn |
| | | | | 85 | | | | | 90 | | | | | 95 | |
| Ile | Glu | Leu | Gln | Val | Asp | Val | Arg | Pro | Pro | Thr | Ser | Gly | Asp | Val | Ser |
| | | | 100 | | | | | 105 | | | | | 110 | | |
| Phe | Val | Asp | Phe | Gln | Ala | Thr | Asn | Gly | Ser | Asp | Lys | Leu | Phe | Leu | His |
| | | 115 | | | | | 120 | | | | | 125 | | | |
| Trp | Gly | Ala | Val | Lys | Phe | Gly | Lys | Glu | Thr | Trp | Ser | Leu | Pro | Asn | Asp |
| | 130 | | | | | 135 | | | | | 140 | | | | |
| Arg | Pro | Asp | Gly | Thr | Lys | Val | Tyr | Lys | Asn | Lys | Ala | Leu | Arg | Thr | Pro |
| 145 | | | | | 150 | | | | | 155 | | | | | 160 |
| Phe | Val | Lys | Ser | Gly | Ser | Asn | Ser | Ile | Leu | Arg | Leu | Glu | Ile | Arg | Asp |
| | | | | 165 | | | | | 170 | | | | | 175 | |
| Thr | Ala | Ile | Glu | Ala | Ile | Glu | Phe | Leu | Ile | Tyr | Asp | Glu | Ala | Tyr | Asp |
| | | | 180 | | | | | 185 | | | | | 190 | | |
| Lys | Trp | Ile | Lys | Asn | Asn | Gly | Gly | Asn | Phe | Arg | Val | Lys | Leu | Ser | Arg |
| | | 195 | | | | | 200 | | | | | 205 | | | |
| Lys | Glu | Ile | Arg | Gly | Pro | Asp | Val | Ser | Val | Pro | Glu | Glu | Leu | Val | Gln |
| | 210 | | | | | 215 | | | | | 220 | | | | |
| Ile | Gln | Ser | Tyr | Leu | Arg | Trp | Glu | Arg | Lys | Gly | Lys | Gln | Asn | Tyr | Thr |
| 225 | | | | | 230 | | | | | 235 | | | | | 240 |
| Pro | Glu | Lys | Glu | Lys | Glu | Glu | Tyr | Glu | Ala | Ala | Arg | Thr | Glu | Leu | Gln |
| | | | | 245 | | | | | 250 | | | | | 255 | |
| Glu | Glu | Ile | Ala | Arg | Gly | Ala | Ser | Ile | Gln | Asp | Ile | Arg | Ala | Arg | Leu |
| | | | 260 | | | | | 265 | | | | | 270 | | |
| Thr | Lys | Thr | Asn | Asp | Lys | Ser | Gln | Ser | Lys | Glu | Pro | Leu | His | Val | |
| | | 275 | | | | | 280 | | | | | 285 | | | |
| Thr | Lys | Ser | Glu | Ile | Pro | Asp | Asp | Leu | Ala | Gln | Ala | Gln | Ala | Tyr | Ile |
| | 290 | | | | | 295 | | | | | 300 | | | | |
| Arg | Trp | Glu | Lys | Ala | Gly | Lys | Pro | Asn | Tyr | Pro | Pro | Glu | Lys | Gln | Ile |
| 305 | | | | | 310 | | | | | 315 | | | | | 320 |
| Glu | Glu | Leu | Glu | Glu | Ala | Arg | Arg | Glu | Leu | Gln | Leu | Glu | Leu | Glu | Lys |
| | | | | 325 | | | | | 330 | | | | | 335 | |
| Gly | Ile | Thr | Leu | Asp | Glu | Leu | Arg | Lys | Lys | Ile | Thr | Lys | Gly | Glu | Ile |
| | | | 340 | | | | | 345 | | | | | 350 | | |
| Lys | Thr | Lys | Ala | Glu | Lys | His | Val | Lys | Arg | Ser | Ser | Phe | Ala | Val | Glu |
| | | 355 | | | | | 360 | | | | | 365 | | | |
| Arg | Ile | Gln | Arg | Lys | Lys | Arg | Asp | Phe | Gly | Gln | Leu | Ile | Asn | Lys | Tyr |
| | 370 | | | | | 375 | | | | | 380 | | | | |

```
Pro Ser Ser Pro Ala Val Gln Val Gln Lys Val Leu Glu Glu Pro Pro
385                 390                 395                 400

Ala Leu Ser Lys Ile Lys Leu Tyr Ala Lys Glu Lys Glu Glu Gln Ile
            405                 410                 415

Asp Asp Pro Ile Leu Asn Lys Lys Ile Phe Lys Val Asp Asp Gly Glu
            420                 425                 430

Leu Leu Val Leu Val Ala Lys Ser Ser Gly Lys Thr Lys Val His Ile
            435                 440                 445

Ala Thr Asp Leu Asn Gln Pro Ile Thr Leu His Trp Ala Leu Ser Lys
450                 455                 460

Ser Arg Gly Glu Trp Met Val Pro Pro Ser Ser Ile Leu Pro Pro Gly
465                 470                 475                 480

Ser Ile Ile Leu Asp Lys Ala Ala Glu Thr Pro Phe Ser Ala Ser Ser
            485                 490                 495

Ser Asp Gly Leu Thr Ser Lys Val Gln Ser Leu Asp Ile Val Ile Glu
            500                 505                 510

Asp Gly Asn Phe Val Gly Met Pro Phe Val Leu Leu Ser Gly Glu Lys
            515                 520                 525

Trp Ile Lys Asn Gln Gly Ser Asp Phe Tyr Val Asp Phe Ser Ala Ala
            530                 535                 540

Ser Lys Leu Ala Leu Lys Ala Ala Gly Asp Gly Ser Gly Thr Ala Lys
545                 550                 555                 560

Ser Leu Leu Asp Lys Ile Ala Asp Met Glu Ser Glu Ala Gln Lys Ser
            565                 570                 575

Phe Met His Arg Phe Asn Ile Ala Ala Asp Leu Ile Glu Asp Ala Thr
            580                 585                 590

Ser Ala Gly Glu Leu Gly Phe Thr Gly Ile Leu Val Trp Met Arg Phe
            595                 600                 605

Met Ala Thr Arg Gln Leu Ile Trp Asn Lys Asn Tyr Asn Val Lys Pro
610                 615                 620

Arg Glu Ile Ser Lys Ala Gln Asp Arg Leu Thr Asp Leu Leu Gln Asn
625                 630                 635                 640

Ala Phe Thr Ser His Pro Gln Tyr Arg Glu Ile Leu Arg Met Ile Met
            645                 650                 655

Ser Thr Val Gly Arg Gly Gly Glu Gly Asp Val Gly Gln Arg Ile Arg
            660                 665                 670

Asp Glu Ile Leu Val Ile Gln Arg Lys Asn Asp Cys Lys Gly Gly Met
            675                 680                 685

Met Glu Glu Trp His Gln Lys Leu His Asn Asn Thr Ser Pro Asp Asp
690                 695                 700

Val Val Ile Cys Gln Ala Leu Ile Asp Tyr Ile Lys Ser Asp Phe Asp
705                 710                 715                 720

Leu Gly Val Tyr Trp Lys Thr Leu Asn Glu Asn Gly Ile Thr Lys Glu
            725                 730                 735

Arg Leu Leu Ser Tyr Asp Arg Ala Ile His Ser Glu Pro Asn Phe Arg
            740                 745                 750

Gly Asp Gln Lys Asn Gly Leu Leu Arg Asp Leu Gly His Tyr Met Arg
            755                 760                 765

Thr Leu Lys Ala Val His Ser Gly Ala Asp Leu Glu Ser Ala Ile Ala
            770                 775                 780

Asn Cys Met Gly Tyr Lys Thr Glu Gly Glu Gly Phe Met Val Gly Val
785                 790                 795                 800
```

-continued

```
Gln Ile Asn Pro Val Ser Gly Leu Pro Ser Gly Phe Gln Gly Leu Leu
            805                 810                 815
His Phe Val Leu Asp His Val Glu Asp Lys Asn Val Glu Thr Leu Leu
            820                 825                 830
Glu Gly Leu Leu Glu Ala Arg Glu Glu Leu Arg Pro Leu Leu Leu Lys
            835                 840                 845
Pro Asn Asn Arg Leu Lys Asp Leu Leu Phe Leu Asp Ile Ala Leu Asp
            850                 855                 860
Ser Thr Val Arg Thr Ala Val Glu Arg Gly Tyr Glu Glu Leu Asn Asn
865                 870                 875                 880
Ala Asn Pro Glu Lys Ile Met Tyr Phe Ile Ser Leu Val Leu Glu Asn
            885                 890                 895
Leu Ala Leu Ser Val Asp Asp Asn Glu Asp Leu Val Tyr Cys Leu Lys
            900                 905                 910
Gly Trp Asn Gln Ala Leu Ser Met Ser Asn Gly Gly Asp Asn His Trp
            915                 920                 925
Ala Leu Phe Ala Lys Ala Val Leu Asp Arg Ile Arg Leu Ala Leu Ala
            930                 935                 940
Ser Lys Ala Glu Trp Tyr His His Leu Leu Gln Pro Ser Ala Glu Tyr
945                 950                 955                 960
Leu Gly Ser Ile Leu Gly Val Asp Gln Trp Ala Leu Asn Ile Phe Thr
            965                 970                 975
Glu Glu Ile Ile Arg Ala Gly Ser Ala Ala Ser Leu Ser Ser Leu Leu
            980                 985                 990
Asn Arg Leu Asp Pro Val Leu Arg Lys Thr Ala Asn Leu Gly Ser Trp
            995                 1000                1005
Gln Ile Ile Ser Pro Val Glu Ala Val Gly Tyr Val Val Val Val Asp
  1010                1015                1020
Glu Leu Leu Ser Val Gln Asn Glu Ile Tyr Lys Lys Pro Thr Ile Leu
1025                1030                1035                1040
Val Ala Asn Ser Val Lys Gly Glu Glu Ile Pro Asp Gly Ala Val
            1045                1050                1055
Ala Leu Ile Thr Pro Asp Met Pro Asp Val Leu Ser His Val Ser Val
            1060                1065                1070
Arg Ala Arg Asn Gly Lys Val Cys Phe Ala Thr Cys Phe Asp Pro Asn
            1075                1080                1085
Ile Leu Ala Asp Leu Gln Ala Lys Glu Gly Arg Ile Leu Leu Leu Lys
            1090                1095                1100
Pro Thr Pro Ser Asp Ile Ile Tyr Ser Glu Val Asn Glu Ile Glu Leu
1105                1110                1115                1120
Gln Ser Ser Ser Asn Leu Val Glu Ala Glu Thr Ser Ala Thr Leu Arg
            1125                1130                1135
Leu Val Lys Lys Gln Phe Gly Gly Cys Tyr Ala Ile Ser Ala Asp Glu
            1140                1145                1150
Phe Thr Ser Glu Met Val Gly Ala Lys Ser Arg Asn Ile Ala Tyr Leu
            1155                1160                1165
Lys Gly Lys Val Pro Ser Ser Val Gly Ile Pro Thr Ser Val Ala Leu
            1170                1175                1180
Pro Phe Gly Val Phe Glu Lys Val Leu Ser Asp Asp Ile Asn Gln Gly
1185                1190                1195                1200
Val Ala Lys Glu Leu Gln Ile Leu Thr Lys Lys Leu Ser Glu Gly Asp
            1205                1210                1215
Phe Ser Ala Leu Gly Glu Ile Arg Thr Thr Ile Leu Asp Leu Ser Ala
```

-continued

```
                    1220                1225                1230

Pro Ala Gln Leu Val Lys Glu Leu Lys Glu Lys Met Gln Gly Ser Gly
            1235                1240                1245

Met Pro Trp Pro Gly Asp Glu Gly Pro Lys Arg Trp Glu Gln Ala Trp
        1250                1255                1260

Met Ala Ile Lys Lys Val Trp Ala Ser Lys Trp Asn Glu Arg Ala Tyr
1265                1270                1275                1280

Phe Ser Thr Arg Lys Val Lys Leu Asp His Asp Tyr Leu Cys Met Ala
            1285                1290                1295

Val Leu Val Gln Glu Ile Ile Asn Ala Asp Tyr Ala Phe Val Ile His
            1300                1305                1310

Thr Thr Asn Pro Ser Ser Gly Asp Asp Ser Glu Ile Tyr Ala Glu Val
            1315                1320                1325

Val Arg Gly Leu Gly Glu Thr Leu Val Gly Ala Tyr Pro Gly Arg Ala
            1330                1335                1340

Leu Ser Phe Ile Cys Lys Lys Asp Leu Asn Ser Pro Gln Val Leu
1345                1350                1355                1360

Gly Tyr Pro Ser Lys Pro Ile Gly Leu Phe Ile Lys Arg Ser Ile Ile
            1365                1370                1375

Phe Arg Ser Asp Ser Asn Gly Glu Asp Leu Glu Gly Tyr Ala Gly Ala
            1380                1385                1390

Gly Leu Tyr Asp Ser Val Pro Met Asp Glu Glu Lys Val Val Ile
            1395                1400                1405

Asp Tyr Ser Ser Asp Pro Leu Ile Thr Asp Gly Asn Phe Arg Gln Thr
    1410                1415                1420

Ile Leu Ser Asn Ile Ala Arg Ala Gly His Ala Ile Glu Glu Leu Tyr
1425                1430                1435                1440

Gly Ser Pro Gln Asp Ile Glu Gly Val Val Arg Asp Gly Lys Ile Tyr
            1445                1450                1455

Val Val Gln Thr Arg Pro Gln Met
            1460
```

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence:
      Partial sequence

<400> SEQUENCE: 3

```
Asp Lys Ala Ala Glu Thr
1               5
```

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence:
      Partial sequence

<400> SEQUENCE: 4

```
Ile Ala Asp Met Glu
1               5
```

<210> SEQ ID NO 5
<211> LENGTH: 6
<212> TYPE: PRT

```
<213> ORGANISM: Artificial Sequence
<220> FEATURE:
<223> OTHER INFORMATION: Description of Artificial Sequence:
      Partial sequence

<400> SEQUENCE: 5

Val Trp Met Arg Phe Met
 1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence:
      Partial sequence

<400> SEQUENCE: 6

Met Gln Glu Trp His Gln
 1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence:
      Partial sequence

<400> SEQUENCE: 7

Leu Gly His Tyr Met
 1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence:
      Partial sequence

<400> SEQUENCE: 8

Glu Arg Gly Tyr Glu Glu
 1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence:
      Partial sequence

<400> SEQUENCE: 9

Lys Ala Val Leu Asp Arg
 1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence:
      Partial sequence

<400> SEQUENCE: 10

Leu Ser Ser Leu Leu
 1               5
```

```
<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence:
      Partial sequence

<400> SEQUENCE: 11

Ile Pro Asp Gly Ala Val
  1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence:
      Partial sequence

<400> SEQUENCE: 12

Lys Val Cys Phe Ala Thr
  1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence:
      Partial sequence

<400> SEQUENCE: 13

Ile Ser Ala Asp Glu Phe
  1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence:
      Partial sequence

<400> SEQUENCE: 14

Pro Phe Gly Val Phe Glu
  1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence:
      Partial sequence

<400> SEQUENCE: 15

Ser Ser Gly Asp Asp
  1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence:
      Partial sequence
```

-continued

```
<400> SEQUENCE: 16

Ser Phe Ile Cys Lys Lys
 1               5
```